US007794731B2

United States Patent
Mizel et al.

(10) Patent No.: US 7,794,731 B2
(45) Date of Patent: Sep. 14, 2010

(54) **USE OF FLAGELLIN IN THE IMMUNOTHERAPY OF *YERSINIA PESTIS***

(75) Inventors: Steven B. Mizel, Lewisville, NC (US); Anna Nichole Honko, Fort Mills, SC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 3 days.

(21) Appl. No.: 11/793,159

(22) PCT Filed: Dec. 16, 2005

(86) PCT No.: PCT/US2005/045954

§ 371 (c)(1),
(2), (4) Date: Feb. 1, 2008

(87) PCT Pub. No.: WO2006/066214

PCT Pub. Date: Jun. 22, 2006

(65) Prior Publication Data

US 2008/0124361 A1 May 29, 2008

Related U.S. Application Data

(60) Provisional application No. 60/636,635, filed on Dec. 16, 2004, provisional application No. 60/709,609, filed on Aug. 19, 2005.

(51) Int. Cl.
| | |
|---|---|
| A61K 39/02 | (2006.01) |
| A61K 39/116 | (2006.01) |
| A61K 39/00 | (2006.01) |
| A61K 45/00 | (2006.01) |
| A61K 39/38 | (2006.01) |
| A61K 38/00 | (2006.01) |
| C07K 14/00 | (2006.01) |

(52) U.S. Cl. ............. 424/234.1; 424/192.1; 424/190.1; 424/203.1; 424/184.1; 424/282.1; 424/242.1; 514/2; 530/350; 530/825; 530/806

(58) Field of Classification Search ........................ None
See application file for complete search history.

(56) References Cited

U.S. PATENT DOCUMENTS

| | | | | |
|---|---|---|---|---|
| 4,886,748 | A | 12/1989 | Asaka et al. ................ 435/69.7 |
| 5,618,533 | A | 4/1997 | Flavell et al. ............. 424/184.1 |
| 5,888,810 | A | 3/1999 | Meinersmann et al. ... 435/320.1 |
| 5,985,285 | A | 11/1999 | Titball et al. .............. 424/234.1 |
| 6,130,082 | A | 10/2000 | Majarian et al. |
| 6,585,980 | B1 | 7/2003 | Chan et al. ..................... 514/44 |
| 6,638,510 | B1 | 10/2003 | Brubaker et al. .......... 424/184.1 |
| 6,706,522 | B1 | 3/2004 | Blattner et al. .............. 435/325 |
| 2003/0044429 | A1 | 3/2003 | Aderem et al. |
| 2003/0175287 | A1* | 9/2003 | Medzhitov et al. ....... 424/185.1 |
| 2004/0203051 | A1 | 10/2004 | Simard et al. |
| 2008/0003237 | A1 | 1/2008 | Berger et al. |

FOREIGN PATENT DOCUMENTS

| | | |
|---|---|---|
| WO | WO 96/28551 | 9/1996 |
| WO | WO 2007/125535 | 11/2007 |

OTHER PUBLICATIONS

Tikhomirova et al. Zh. Mikrobiol. Epidemiol. Immunobiol. 1:51-55, Jan.-Feb. 2003.*
Westerlund-Wikstrom et al. Protein Engineering 10: 1319-1326, 1997.*
Tanskanen et al. Appl. Environment. Microbiol. 66: 4152-4156, Sep. 2000.*
Eaves-Pyles T.D. et al. *Salmonella* flagellin-dependent proinflammatory responses are localized to the conserved amino and carboxyl regions of the protein, J. Immunol. 2001, vol. 167, pp. 7009-7016.
International Search Report, PCT/US2005/045954, Oct. 16, 2006.
Cuadros et al., "Flagellin Fusion Proteins as Adjuvants or Vaccines Induce Specific Immune Responses", Infection and Immunity 72:5, pp. 2810-2816 (May 2004) XP-002392967.
Newton et al., "Expression and immunogenicity of an 18-residue epitope of HIV1 gp41 inserted in the flagellar protein of a *Salmonella* live vaccine", Research in Microbiology 146:3, pp. 203-216 (1995) XP-002496870.
Newton et al., "Immune Response to Cholera Toxin Epitope Inserted in *Salmonella* Flagellin", Science (Washington DC) 244:4900, pp. 70-72 (1989) XP-001094029.
Extended European Search Report which includes the Supplementary European Search Report and European Search Opinion corresponding to European Application No. EP05854630.0 (5 pages); Dated: Oct. 6, 2008.
Extended European Search Report which includes the Supplementary European Search Report and European Search Opinion corresponding to European Application No. EP05857121.7 (5 pages); Dated: Oct. 7, 2008.
Honko et al., "Flagellin is an Effective Mucosal Adjuvant in the Development of a Protective Immune Response Against *Yersinia pestis*", Abstract of the Eighth Annual Conference on Vaccine Research—Baltimore, MD (May 9-11, 2005).
Honko et al, "Flagellin is an Effective Mucosal Adjuvant in the Development of a Protective Immune Response Against *Yersinia pestis*", Anthrax: The Biotechnology of Biodefense Symposium, Winston, Salem, NC (May 26, 2005).
Honko et al., "Effects of Flagellin on Innate and Adaptive Immunity in the Mouse Lung", Abstract for the 12th International Congress of Immunology—Montreal, Canada (Jul. 18-24, 2004).

(Continued)

*Primary Examiner*—S. Devi
(74) *Attorney, Agent, or Firm*—Myers Bigel Sibley & Sajovec, PA

(57) ABSTRACT

The invention provides a fusion protein comprising a flagellin adjuvant and a *Yersinia pestis* antigen. Also provided are compositions comprising a flagellin adjuvant and a *Yersinia pestis* antigen. The invention also discloses methods of making a fusion protein comprising a flagellin adjuvant and a *Yersinia pestis* antigen. The invention further provides pharmaceutical formulations and methods for inducing an immune response against *Yersinia pestis*.

21 Claims, 8 Drawing Sheets

OTHER PUBLICATIONS

Murthy et al., "Identification of Conserved Domains in *Salmonella muenchen* Flagellin That Are Essential for Its Ability to Activate TLR5 and to Induce an Inflammatory Response in Vitro", Journal of Biological Chemistry, vol. 279:7, pp. 5667-5675 (Feb. 13, 2004).

Verma et al., "Roles of Specific Amino Acids in the N Terminus of *Pseudomonas aeruginosa* Flagellin and of Flagellin Glycosylation in the Innate Immune Response", Infection And Immunity, vol. 73:12, pp. 8237-8246 (Dec. 2005).

Davila et al., "Repeated Administration of Cytosine-Phosphorothiolated Guanine-Containing Oligonucleotides Together with Peptide/Protein Immunization Results in Enhanced CTL Responses with Anti-Tumor Activity", The Journal of Immunology, vol. 165, pp. 539-547 (2000).

Brunner et al., "Enhanced Dendritic Cell Maturation by TNF-α or Cytidine-Phosphate-Guanosine DNA Drives T Cell Avtivation In Vitro and Therapeutic Anti-Tumor Immune Responses In Vivo", The Journal of Immunology, vol. 165, pp. 6278-6286 (2000).

Donnelly et al., "Two Nonadjacent Regions in Enteroaggregative *Escherichia coli* Flagellin Are Required for Activation of Toll-like Receptor 5", The Journal of Biological Chemistry, vol. 277:43, pp. 40456-40461 (2002).

McDermott et al., "High-Affinity Interaction between Gram-Negative Flagellin and a Cell Surface Polypeptide Results in Human Monocyte Activation", Infection And Immunity, vol. 68:10, pp. 5525-5529 (Oct. 2000).

Honko et al., "Mucosal Administration of Flagellin Induces Innate Immunity in the Mouse Lung", Infection And Immunity, vol. 72:11, pp. 6676-6679 (Nov. 2004).

Cornelis, "Molecular and cell biology aspects of plague", Colloquium, vol. 97:16, pp. 8778-8783 (Aug. 1, 2000).

Liaudet et al., "The Flagellin—TLR5 Axis: Therapeutic Opportunities", Drug News Perspect, vol. 15:7, pp. 1-13 (Sep. 2002).

Mizel et al., "Induction of Macrophage Nitric Oxide Production by Gram-Negative Flagellin Involves Signaling Via Heteromeric Toll-Like Receptor 5/Toll-Like Receptor 4 Complexes", The Journal of Immunology, vol. 170, pp. 6217-6223 (2003).
McSorley et al., "Bacterial Flagellin Is an Effective Adjuvant for $CD4^+$ T Cells In Vivo", The Journal of Immunology, vol. 169, pp. 3914-3919 (2002).
Ciacci-Woolwine et al., "*Salmonella* Flagellin Induces Tumor Necrosis Factor Alpha in a Human Promonocytic Cell Line", Infection And Immunity, vol. 66:3, pp. 1127-1134 (Mar. 1998).

Moors et al., "Activation of Interleukin-1 Receptor-Associated Kinase by Gram-Negative Flagellin", Infection And Immunity, vol. 69:7, pp. 4424-4429 (Jul. 2001).

Gewirtz et al., "*Salmonella typhimurium* translocates flagellin across intestinal epithelia, inducing a proinflamatory response", The Journal of Clinical Investigation, vol. 107:1, pp. 99-109 (Jan. 2001).

Steiner et al., "Enteroaggregative *Escherichia coli* expresses a novel flagellin that causes IL-8 release from intestinal epithelial cells", The Journal of Clinical Investigation, vol. 105:12, pp. 1769-1777 (Jun. 2000).

Eaves-Pyles et al., "Flagellin, a Novel Mediator of *Salmonella*-Induced Epithelial Activation and Systemic Inflammation: IκBα Degradation, Induction of Nitric Oxide Synthase, Induction of Proinflammatory Mediators, and Cardiovascular Dysfunction", The Journal of Immunology, vol. 166, pp. 1248-1260 (2001).

Liaudet et al., "Flagellin From Gram-Negative Bacteria Is A Potent Mediator Of Acute Pulmonary Inflammation In Sepsis", SCHOCK, vol. 19:2, pp. 131-137 (2003).

Liaudet et al., "Comparison of Inflammation, Organ Damage, and Oxidant Stress Induced by *Salmonella enterica* Serovar Muenchen Flagellin and Serovar Enteritidis Lipopolysaccharide", Infection And Immunity, vol. 70:1, pp. 192-198 (Jan. 2002).

McEwen et al., "Synthetic recombinant vaccine expressing influenza haemagglutinin epitope in *Salmonella* flagellin leads to partial protection in mice", Vaccine, col. 10:6, pp. 405-411 (1992).

Levi et al., "Synthetic recombinant influenza vaccine induces efficient long-term immunity and cross-strain protection", Vaccine, vol. 14:1 (1996).

Ben-Yedidia et al., "Effect of pre-existing carrier immunity on the efficacy of synthetic influenza vaccine", Immunology Letters, vol. 64, pp. 9-15 (1998).

Luo et al., "Transcription factor Fos-related antigen 1 is an effective target for a breast cancer vaccine", PNAS, vol. 100:15, pp. 8850-8855 (Jul. 22, 2003).

Jeon et al., "Intranasal immunization with synthetic recombinant vaccine containing multiple epitopes of influenza virus", Vaccine, vol. 20, pp. 2772-2780 (2002).

Smith et al., "Toll-like receptor 5 recognizes a conserved site on flagellin required for protofilament formation and bacterial motility", Nature Immunology, vol. 4:12, pp. 1247-1253 (Dec. 2003).

Anderson Jr. et al., "Protection Of Mice From Fatal Bubonic and Pneumonic Plague By Passive Immunization With Monoclonal Antibodies Against the F1 Protein Of *Yersinia pestis*", Am. J. Trop. Med. Hyg., vol. 56:4, pp. 471-473 (1997).

Andrews et al., "Fraction 1 Capsular Antigen (F1) Purification from *Yersinia pestis* CO92 and from an *Escherichia coli* Recombinant Strain and Efficacy against Lethal Plague Challenge", Infection And Immunity, vol. 64:6, pp. 2180-2187 (Jun. 1996).

Eyles et al., "Immunisation against plague by transcutaneous and intradermal application of subunit antigens", Vaccine, vol. 22, pp. 4365-4373 (2004).

Eyles et al., "Intra nasal administration of poly-lactic acid microsphere co-encapsulated *Yersinia pestis* subunits confers protection from pneumonic plague in the mouse", Vaccine, vol. 16:7, pp. 698-707 (1998).
Eyles et al., "Analysis of local and systemic immunological responses after intra-tracheal, intra-nasal and intra-muscular administration of microsphere co-encapsulated *Yersinia pestis* sub-unit vaccines", Vaccine, vol. 16:20, pp. 2000-2009 (1998).
Glynn et al., "Effect of homologous and heterologous prime-boost on the immune response to recombinant plague antigens", Vaccine, vol. 23, pp. 1957-1965 (2005).
Grosfeld et al., "Effective Protective Immunity to *Yersinia pestis* Infection Conferred by DNA Vaccine Coding for Derivatives of the F1 Capsular Antigen", Infection And Immunity, vol. 71:1, pp. 374-383 (Jan. 2003).
Heath et al., "Protection against experimental bubonic and pneumonic plague by a recombinant capsular F1-V antigen fusion protein vaccine", Vaccine, vol. 16:11/12, pp. 1131-1137 (1998).
Leary et al., "Expression of an F1/V fusion protein in attenuated *Salmonella typhimurium* and protection of mice against plague", Microbial Pathogenesis, vol. 23, pp. 167-179 (1997).
Motin et al., "Passive Immunity to *Yersiniae* Mediated by Anti-Recombinant V Antigen and Protein A-V Antigen Fusion Peptide", Infection And Immunity, vol. 62:10, pp. 4192-4201 (Oct. 1994).
Pasare et al., "Toll-Dependent Control Mechanisms of CD4 T Cell Activation", Immunity, vol. 21, pp. 733-741 (Nov. 2004).
Simpson et al., "Recombinant Capsular Antigen (Fraction 1) From *Yersinia pestis* Induces A Protective Antibody Response In BALB/C Mice", Am. J. Trop. Med. Hyg., vol. 43:4, pp. 389-396 (1990).
Wang et al., "A DNA vaccine producing LcrV antigen in oligomers is effective in protecting mice from lethal mucosal challenge of plague", Vaccine, vol. 22, pp. 3348-3357 (2004).
Williamson et al., "Human Immune Response to a Plague Vaccine Comprising Recombinant F1 and V Antigens", Infection And Immunity, vol. 73:6, pp. 3598-3608 (Jun. 2005).
Williamson et al., "An IgG1 titre to the F1 and V antigens correlates with protection against plague in the mouse model", Clin. Exp. Immunol. vol. 116, pp. 107-114 (1999).
Williamson et al., "A single dose sub-unit vaccine protects against pneumonic plague", Vaccine, vol. 19, pp. 566-571 (2001).
Andersen-Nissen et al. "Evasion of Toll-Like Receptor 5 by Flagellated Bacteria" *PNAS* 102(26):9247-9252 (2005).
Hayashi et al. "The innate immune response to bacterial flagellin is mediated by Toll-like receptor 5" *Nature* 410:1099-1103 (2001).
Macnab. "How Bacteria Assemble Flagella" *Annu. Rev. Microbiol.* 57:77-100 (2003).

* cited by examiner

FIG. 7

USE OF FLAGELLIN IN THE IMMUNOTHERAPY OF *YERSINIA PESTIS*

RELATED APPLICATION INFORMATION

This application is a national phase application of PCT Application PCT/US2005/045954 filed 16 Dec. 2005, and published in English on 22 Jun. 2006 as International Publication No. WO 2006/066214, and which claims the benefit of U.S. Provisional Application Ser. No. 60/636,635, filed 16 Dec. 2004, and U.S. Provisional Application Ser. No. 60/709,609, filed 19 Aug. 2005; the disclosures of which are incorporated herein by reference in their entireties.

STATEMENT OF FEDERAL SUPPORT

This invention was made with government support under grant numbers R01-AI051319, P01-AI1060642 and T32-AI007401 from the National Institutes of Health. The United States government has certain rights to this invention.

FIELD OF THE INVENTION

The present invention concerns the use of a flagellin adjuvant, antigens from *Yersinia pestis* and fusion proteins thereof to produce an immune response against *Y. pestis* (e.g., in the prophylactic treatment of *Y. pestis* infection).

BACKGROUND OF THE INVENTION

Although the shift in vaccine development from complete pathogens to individual antigens has led to safer vaccines, efficacy has been markedly reduced. Vaccine adjuvants promote strong adaptive responses to soluble recombinant protein antigens. The proinflammatory effects of toll-like receptor (TLR) agonists such as gram-negative LPS and bacterial CpG DNA has led to evaluation of their adjuvant properties and effects on dendritic cells (Jäger et al. (2002) *Curr. Opin. Immunol.* 14:178-182; Ko et al. (2003) *Clin. Cancer res.* 9:3222-3234; Medzhitov (2001) *Nat. Immunol.* 1:135-145). Most TLR agonists function as adjuvants by stimulating the production of cytokines and the maturation of dendritic cells, thereby linking innate and adaptive immunity.

*Yersinia pestis*, the causative agent of plague, is a gram-negative organism responsible for approximately 200 millions deaths during three major pandemics. In humans, plague has three forms designated by the nature of the infection: bubonic, pneumonic and septicemic. Whereas bubonic plague is spread via bites from infected fleas, the pneumonic form may be transmitted person-to-person. Without medical treatment, pneumonic plague is a rapidly progressing disease with a mortality rate approaching 100% (McSorley et al. (2002) *J. Immunol.* 169:3914-3919; Means et al. (2003) *J. Immunol.* 170:5165-5175).

The use of whole-cell vaccines for plague has raised safety concerns. Immunization with the F1 antigen of *Y. pestis* and an appropriate adjuvant elicits a protective response that correlates with the titer of anti-F1 IgG antibodies (Davila and Celis (2000) *J. Immunol.* 165:539-547; Brunner et al. (2000) *J. Immunol.* 165:6278-6286). A synergistic protective effect is obtained when animals are immunized with both F1 and V antigens or a recombinant F1/V fusion protein (Ciacci-Woolwine et al. (1998) *Infect. Immun.* 66:1127-1134; Moors et al. (2001) *Infect. Immun.* 69:4424-4429; Gewirtz et al. (2001) *J. Clin. Invest.* 107:99-109; Steiner et al. (2000) *J. Clin. Invest.* 105:1769-1777). Although highly variable responses were observed, a phase 1 clinical trial demonstrated that intramuscular immunization with a vaccine containing F1 and V is immunogenic in humans (Eaves-Pyles et al. (2001) *J. Immunol.* 1666:1248-1260).

It would be desirable to provide improved reagents, pharmaceutical formulations and methods for producing immune responses against pathogens such as *Y. pestis*.

SUMMARY OF THE INVENTION

A first aspect of the invention is a fusion protein comprising, consisting of, or consisting essentially of: (a) a flagellin adjuvant comprising, consisting of, or consisting essentially of (i) a flagellin N-terminal constant region; (ii) a flagellin C-terminal constant region; and (b) a *Yersinia pestis* antigen between the N-terminal constant region and the C-terminal constant region (e.g., inserted into or in place of part or all of the flagellin hypervariable region, which is optionally partially or entirely deleted).

A further aspect of the invention is a nucleic acid encoding a fusion protein as described above. In some embodiments, the nucleic acid is operably associated with a promoter.

A further aspect of the invention is a vector comprising a nucleic acid as described above.

A further aspect of the invention is a host cell comprising a nucleic acid or vector as described above. In some embodiments, the host cell expresses the encoded fusion protein.

A further aspect of the invention is a method of making a fusion protein as described above, the method comprising culturing a host cell comprising a nucleic acid encoding the fusion protein described above in a suitable culture medium under conditions sufficient for the fusion protein to be production. Optionally, the fusion protein is collected from the host cell or from the culture medium.

A further aspect of the invention is a composition (e.g., for mucosal delivery) comprising, consisting of, or consisting essentially of (a) a flagellin adjuvant, and (b) a *Yersinia pestis* antigen (with the *Y. pestis* antigen and the flagellin adjuvant being separate or coupled to one another, i.e., in the form of a fusion protein, for example, a fusion protein as described herein).

A further aspect of the present invention is a pharmaceutical formulation comprising a fusion protein or a composition as described above in a pharmaceutically acceptable carrier.

A further aspect of the invention is a method of inducing an immune response (e.g., producing antibodies and/or inducing a cell-mediated immune response) to a *Y. pestis* antigen in a subject, comprising administering a fusion protein, a composition, or a pharmaceutical formulation as described above to the subject in an amount effective to induce an immune response to the *Y. pestis* antigen in the subject.

A still further aspect of the invention is a method of treating a subject for a *Y. pestis* infection (e.g., vaccinating a patient against a *Y. pestis* infection) comprising administering a fusion protein, a composition, or a pharmaceutical formulation as described above to the subject in an amount effective to treat *Y. pestis* infection (e.g., to produce a prophylactic protective immune response and/or to produce a protective immune response against a *Y. pestis* infection in the subject).

In particular embodiments of the methods of the invention, the subject is a mammalian subject, a primate subject, or a human subject.

A further aspect of the invention is the use of a fusion protein or composition as described herein for the preparation of a medicament for carrying out a method of treatment as described herein.

These and other aspects of the invention are set forth in the description of the invention that follows.

BRIEF DESCRIPTION OF THE DRAWINGS

Figure 7:
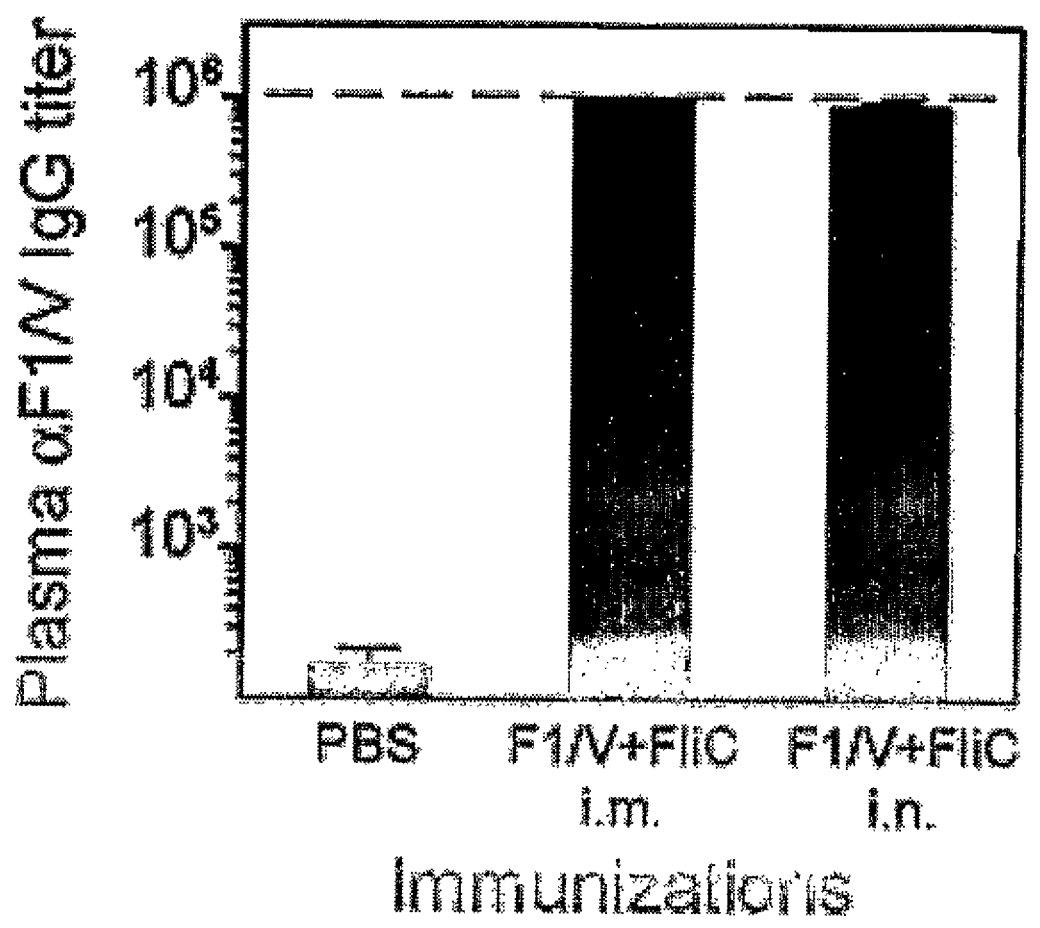

FIG. 7 shows that flagellin is an effective adjuvant in non-human primates. Female cynomolgus monkeys (Macaca fascicularis) were immunized intranasally (n=6) or intramuscularly (n=6) with 150 µg F1/V fusion protein+50 µg flagellin. Control animals (n=3) were immunized i.n. and i.m. with PBS alone. No significant change in body temperature occurred over 12 h and TNF-α"was not detected in plasma collected at 4 h, 12 h and 24 h post-immunization. Animals were boosted in an identical manner at 4 weeks and plasma was collected 2 weeks later for analysis by ELISA. Bars indicate mean anti-F1/V antibody titers±s.e.m. and * indicates statistical significance over intranasal immunization ($p<0.006$).

DETAILED DESCRIPTION OF THE PREFERRED EMBODIMENTS

Figure 1:
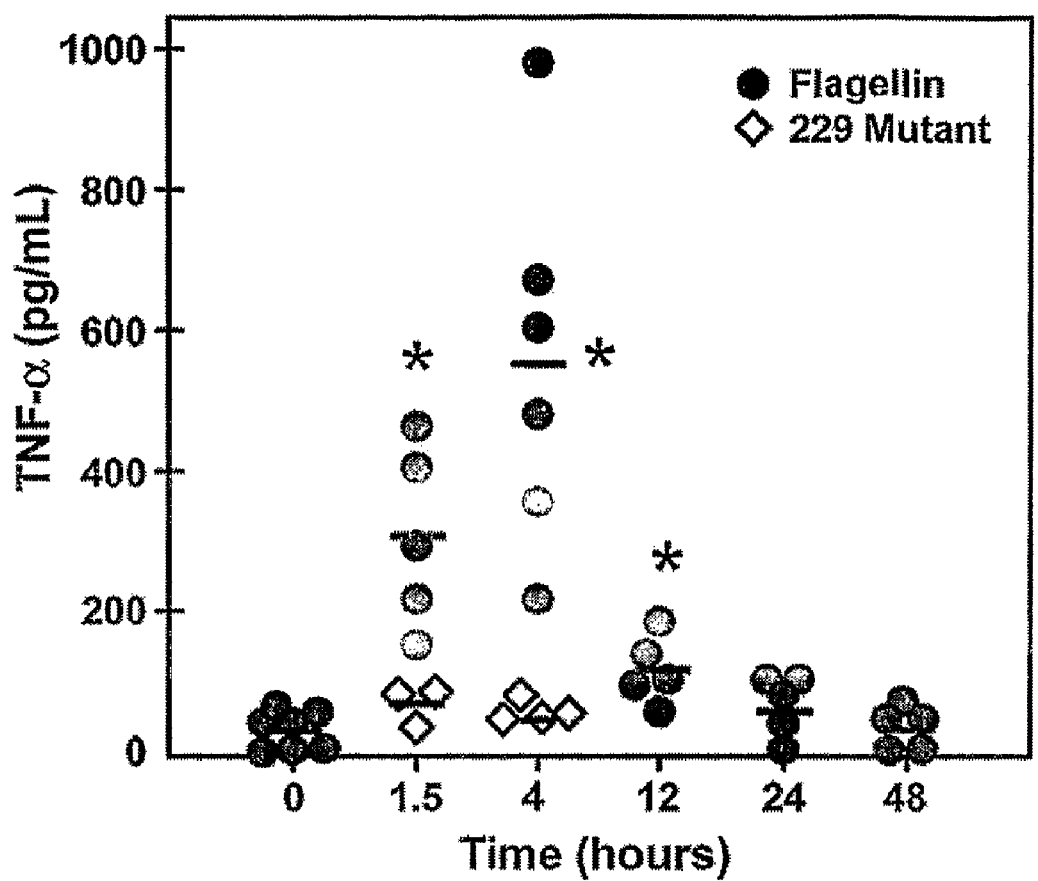
FIG. 1 depicts TNFα"expression in the lungs of BALB/c mice given flagellin or mutant flagellin 229 by i.t. instillation.
Figure 2:
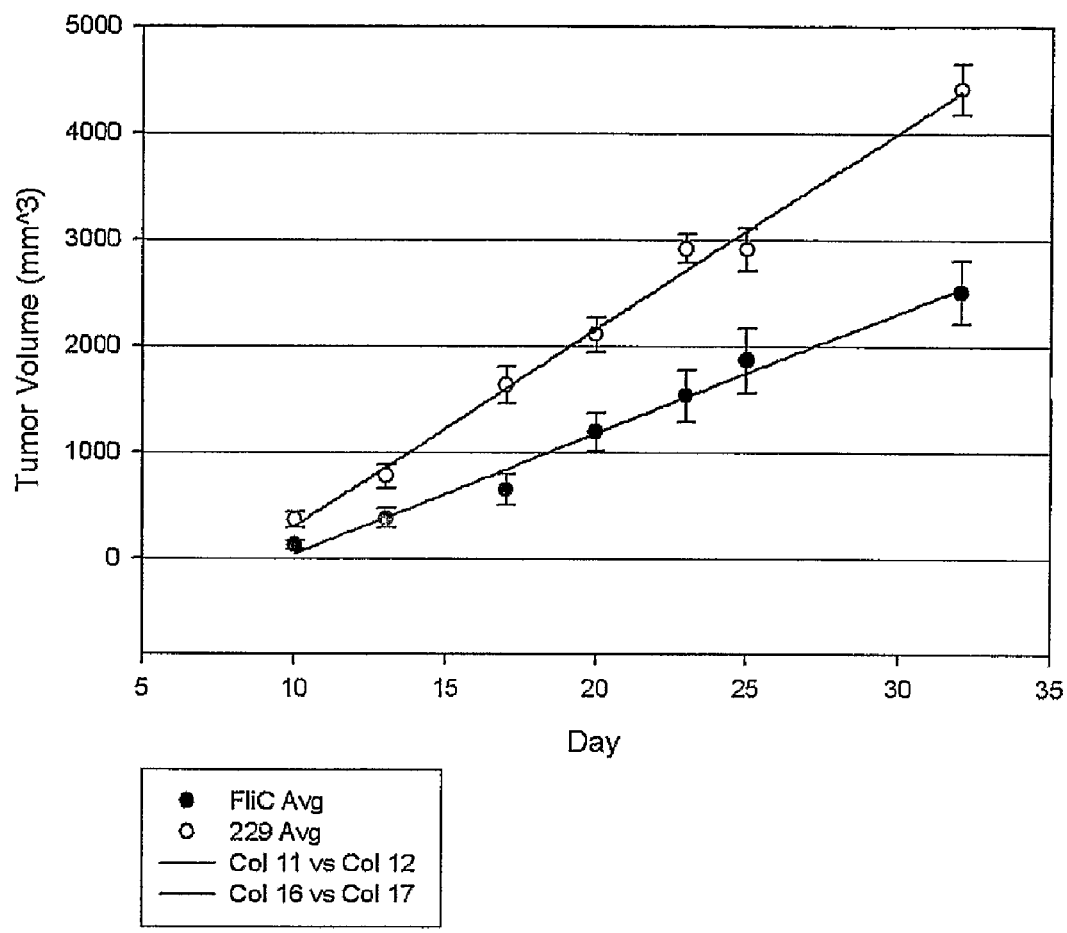
FIG. 2 depicts the effect of flagellin on tumor growth. The open circles represent the mice given the Fra-1 antigen and the inactive form of flagellin. The closed circles represent the mice given Fra-1 antigen and the active form of flagellin.

The present invention is based, in part, on the discovery that flagellins, and fragments thereof, can function as adjuvants, including as mucosal adjuvants, to enhance the immune response mounted in a subject against Yersinia pestis.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

As used in the description of the invention and the appended claims, the singular forms "a,""an""and "the""are intended to include the plural forms as well, unless the context clearly indicates otherwise.

By "consisting essentially of""as used herein, it is meant that the indicated peptide, protein, fusion protein, nucleic, compound, composition, and the like does not include any other material elements (i.e., elements that materially impact the structure and/or function of the peptide, protein, fusion protein, nucleic acid, compound or composition).

In representative embodiments of the invention, the peptides, proteins, fusion proteins, nucleic acids and/or cells of the invention are "isolated." By "isolated" it is meant that the peptide, protein, fusion protein, nucleic acid and/or cell is at least partially purified away from other components.

1. *Yersinia pestis* Antigens.

The terms "immunogen" and "antigen" are used interchangeably herein and mean any compound (including peptides and proteins) to which a cellular and/or humoral immune response can be directed.

The present invention can be practiced with any suitable *Y. pestis* antigen. Antigens obtained from *Y. pestis* that can be used to carry out the present invention are known and described in, for example, U.S. Pat. Nos. 6,706,522; 6,638,510; and 5,985,285. In particular embodiments, the antigen is a *Y. pestis* V antigen and/or a *Y. pestis* F1 antigen (these terms including the entire protein and fragments thereof, which may be at least about 10, 15, 20, 30, or 50 contiguous amino acids in length), such as described in U.S. Pat. No. 5,985,285; or fusions of the *Y. pestis* V antigen and F1 antigens (again, these terms including the entire protein and fragments thereof, which may be at least about 10, 15, 20, 30 or 50 contiguous amino acids in length). In some embodiments, the antigen comprises all or a fragment of a mature *Y. pestis* V protein and/or F1 protein or, alternatively, can comprise all or a fragment of a *Y. pestis* V and/or F1 precursor. Suitable fragments comprise one or more epitopes that induce an immune response and, optionally, confer protection. In representative embodiments, the fragment comprises all or part of the extracellular portion of the protein. Further, as used herein, a "*Y. pestis* antigen" or "antigen from *Y. pestis*" or like terms include, without limitation, naturally occurring *Y. pestis* antigens and modified forms thereof that induce an immune response in a subject, optionally a protective immune response. For example, the native antigen can be modified to increase safety and/or immunogenicity.

*Y. pestis* antigens may be in the form of a fusion peptide, such as an F1/V fusion peptide or a V/F1 fusion peptide, including but not limited to those described in U.S. Pat. No. 5,985,285 to Titball et al., and S. Leary et al., (1997) *Microbial Pathogenesis* 23:167-179. Where two antigens are joined as a fusion peptide, they may be joined directly to one another or joined by a peptide linking or "hinge" segment (e.g., a segment of 2, 3, 4, 6, 8, 10, 15, 20, 30, 50 or more amino acids).

2. Flagellins.

The inventor has determined that flagellin can function as an adjuvant, including acting as a mucosal adjuvant, to enhance the active immune response mounted by a host to a *Y. pestis* antigen. As used herein, the term "adjuvant" has its ordinary meaning as understood by those skilled in the art. For example, an adjuvant can be defined as a substance that increases the ability of an antigen to stimulate an immune response against the antigen in the subject. In particular embodiments, the adjuvant increases the immune response against the antigen by at least about 2, 3, 4, 5, 10, 15, 20, 30, 40, 50, 60, 75, 100, 150, 500, 1000-fold or more. In other embodiments, the adjuvant reduces the amount of antigen required to achieve a particular level of immune response (cellular and/or humoral and/or mucosal), e.g., a reduction of at least about 15%, 25%, 35%, 50%, 65%, 75%, 80%, 85%, 90%, 95%, 98% or more. An adjuvant can further be a substance that prolongs the time over which an immune response, optionally protective immune response, is sustained (e.g., by at least about a 2-fold, 3-fold, 5-fold, 10-fold, 20-fold longer time period or more). In some instances there may be no significant immune response elicited in the host in the absence of an adjuvant.

Flagellin proteins are known and described, for example, in U.S. Pat. Nos. 6,585,980, 6,130,082; 5,888,810; 5,618,533; 4,886,748 and U.S. Patent Publication No. US 2003/0044429 A1; and Donnelly et al., (2002) *J. Biol. Chem.* 43:40456. Most gram-negative bacteria express flagella, which are surface structures that provide motility. The flagella are formed from a basal body, a filament, and a hook that connects the two. The filament is formed of a long polymer of a single protein, flagellin, with a small cap protein at the end. Polymerization of flagellin is mediated by conserved regions at the N- and C-termini, whereas the intervening regions of the flagellin protein are very diverse among species.

In illustrative embodiments of the invention, a fusion protein is provided comprising a flagellin adjuvant and one or more *Y. pestis* antigens. In general, fusion proteins of the invention comprise, consist essentially of, or consist of: (a) a flagellin adjuvant comprising (i) a flagellin N-terminal constant region; and (ii) a flagellin C-terminal constant region; and (b) a *Y. pestis* antigen, wherein the *Y. pestis* antigen is between the N-terminal constant region and the C-terminal constant region. In some embodiments, the flagellin hypervariable region between the constant regions is deleted (in whole or in part); in other embodiments the hypervariable region is present. When the hypervariable region is present (in whole or in part) the antigen can be inserted (i) within the hypervariable region, (ii) between the flagellin N-terminal constant region and the hypervariable region, or (iii) between the flagellin C-terminal constant region and the hypervariable region.

Further, the N-terminal constant and C-terminal constant regions can be linked by a hinge region. The hypervariable region or a *Y. pestis* antigen can function as a hinge region. Additionally, or alternatively, a segment of about 2, 3, 4, 6, 8, 10, 15, 20, 30, 50 or more amino acids can function as a hinge region.

Conserved regions of flagellin are well known in the art and have been described, for example, in Mimori-Kiyosue et al., (1997) *J. Mol. Virol.* 270:222-237; Iino et al., (1977) *Ann. Rev. Genet.* 11:161-182; and Schoenhals et al, (1993) *J. Bacteriol.* 175:5395-5402. As is understood by those skilled in the art, the size of the constant region will vary somewhat depending on the source of the flagellin protein. In general, the N-terminal constant domain includes the approximately 170 or 180 N-terminal amino acids of the protein, whereas the C-terminal constant domain typically spans the approximately 85 to 100 C-terminal amino acids. The central hypervariable region varies considerably by size and sequence among bacteria, and accounts for most of the difference in molecular mass. The N- and C-terminal constant regions of flagellin proteins from a variety of bacteria are known, and others can be readily identified by those skilled in the art using known alignment techniques, which are facilitated by the elucidation of the crystal structure of the flagellin monomer (Samatey et al., (2001) *Nature* 41:331).

The terms "flagellin N-terminal constant region" and "flagellin C-terminal constant region" as used herein includes active fragments (e.g., fragments of at least about 50, 100 or 120 amino acids in length) and modifications of any of the foregoing that enhance the immune response to the *Y. pestis* antigen (e.g., by activating the TLR5 pathway). For example, the native flagellin regions can be modified to increase safety and/or immune response. In some embodiments, the flagellin N-terminal and/or C-terminal constant region comprises the full-length region or, alternatively, can comprise only a fragment of one or both regions.

In particular embodiments, the N-terminal and/or C-terminal constant region comprises a TLR5 recognition site(s) and is able to activate the TLR5 pathway.

In representative embodiments, the N-terminal constant region comprises the N-terminal RINSA domain (amino acids 31-52 of the *S. dublin* flagellin) as described by Eaves-Pyles et al. (2001) *J. Immunology* 167:7009-7016, or a homolog or modified form thereof that enhances the immunogenicity of the *Y. pestis* antigen. In other embodiments, the N-terminal constant region comprises the D1 and D2 domains, and the C-terminal constant region comprises the D1 and D2 domains (Eaves-Pyles et al. (2001) *J. Immunology* 167:7009-7016) or a modified form thereof that enhances the immunogenicity of the *Y. pestis* antigen.

In other embodiments, the flagellin N-terminal and/or C-terminal constant region comprises, consists of, or consists essentially of the peptide GAVQNRFNSAIT (SEQ ID NO:4) as described by U.S. Patent Publication No. US 2003/0044429 A1 to Alderem et al., or a homolog or modification thereof that enhances the immunogenicity of the *Y. pestis* antigen.

In still other embodiments, the N-terminal constant domain comprises the "motif N" (e.g., amino acids 98-108 of the *S. muenchen* flagellin) and/or the C-terminal constant domain comprises the "motif C""(e.g., amino acids 441-449 of *S. muenchen* flagellin) identified by Kanneganti et al., (2004) *J. Biol. Chem.* 279:5667-5676, or a homolog or modified form thereof that enhances an immune response to the *Y. pestis* antigen.

In other illustrative embodiments, the N-terminal constant domain comprises amino acids 88 to 97 of the *P. aeruginosa* flagellin (see, e.g., Verma et al., (2005) *Infect. Immun.* 73:8237-8246) or a homolog or modified form thereof that enhances an immune response to the *Y. pestis* antigen.

Regions of the flagellin protein involved in TLR5 signaling have been identified by Smith et al. (2003) *Nat. Immunol.* 4:1247-1253 (e.g., amino acids 78-129, 135-173 and 394-444 of *S. typhimurium* flagellin or homologs or modified forms thereof).

The flagellin N-terminal constant, C-terminal constant and hypervariable regions can be derived from flagellins from any suitable source, with some or all of these regions being derived from the same organism or from different organisms. A number of flagellin genes have been cloned and sequenced (see, e.g., Kuwajima et al., (1986) *J. Bact.* 168:1479; Wei et al., (1985) *J. Mol. Biol.* 186:791-803; and Gill et al., (1983) *J. Biol. Chem.* 258:7395-7401). Non-limiting sources of flagellins include but are not limited to *S. enteritidis, S. typhimurium, S. dublin, H. pylori, V. cholera, S. marcesens, S. flexneri, S. enterica, T. pallidun, L. pneumophila, B. burgdorferei, C. difficile, A. tumefaciens, R. meliloti, B. clarridgeiae, R. lupine, P. mirabilis, B. subtilis, P. aeruginosa,* and *E. coli.*

Non-limiting examples of fusion proteins of the invention are provided in the working Examples herein.

Optionally, the fusion protein can comprise any other peptide or protein. For example, the fusion protein can further comprise one or more antigens from other organisms. In representative embodiments, the fusion protein further comprises an immunomodulatory compound. For example, it is known in the art that immune responses can be enhanced by an immunomodulatory cytokine or chemokine (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell growth factor, CD40 Ligand, tumor necrosis factor-α, tumor necrosis factor-β, monocyte chemoattractant protein-1, granulocyte-macrophage colony stimulating factor, lymphotoxin, CCL25 [MECK], and CCL28 [TECH]).

The invention also provides a composition comprising a flagellin adjuvant and a *Y. pestis* antigen. According to this embodiment, the flagellin adjuvant can be a full-length flagellin or can be a flagellin peptide comprising the N-terminal constant and/or C-terminal constant regions as described in more detail above. Further, also as described above, the flagellin adjuvant can be coupled (i.e., fused) to a *Y. pestis* antigen to form a fusion protein. In exemplary embodiments, the *Y. pestis* antigen is a *Y. pestis* F1 protein, a *Y. pestis* V protein, or a fusion thereof. The composition can comprise one or more *Y. pestis* antigens fused to the flagellin adjuvant and, optionally, one or more *Y. pestis* antigens present in the composition are not fused to the flagellin adjuvant. In other embodiments, the flagellin adjuvant is not coupled to a *Y. pestis* antigen.

Unless indicated otherwise, the fusion protein is administered per se as a protein (or a nucleic acid encoding the protein) and not as part of live, killed, or recombinant bacterium- or virus-vectored vaccine.

4. Recombinant Nucleic Acids and Production of Fusion Proteins.

Except as otherwise indicated, standard methods known to those skilled in the art may be used for cloning genes, amplifying and detecting nucleic acids, generating fusion constructs, expressing peptides in host cells or organisms, and the like. Such techniques are known to those skilled in the art. See, e.g., Sambrook et al., "Molecular Cloning""A Laboratory Manual 2nd Ed. (Cold Spring Harbor, N.Y., 1989); F. M. Ausubel et al. Current Protocols in Molecular Biology (Green Publishing Associates, Inc. and John Wiley & Sons, Inc., New York).

As used herein, "nucleic acid""encompasses both RNA and DNA, including cDNA, genomic DNA, synthetic (e.g., chemically synthesized) DNA and chimeras of RNA and DNA. The nucleic acid may be double-stranded or single-stranded. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

The fusion protein of the invention can be produced in, and optionally purified from, cultured cells or organisms expressing a heterologous nucleic acid encoding the fusion protein for a variety of purposes (e.g., to produce immunogenic compositions, as a diagnostic or research reagent, and the like).

In some embodiments, the fusion protein can be collected and, optionally, purified from the host cell. For example, the fusion protein can be collected from the conditioned medium. According to this embodiment, it may be advantageous to express the fusion protein operably associated with a secretory signal sequence. Alternatively, the fusion protein can be isolated from the host cell (e.g., the host cell can be lysed and the fusion protein isolated therefrom).

In other embodiments, the host cells are collected and the fusion protein is not isolated therefrom.

Generally, the heterologous nucleic acid is incorporated into an expression vector (viral or non-viral). Suitable expression vectors include but are not limited to plasmids, bacteriophage, bacterial artificial chromosomes (bacs), yeast artificial chromosomes (yacs), cosmids, virus vectors, and the like. Expression vectors compatible with various host cells are well known in the art and contain suitable elements for transcription and translation of nucleic acids. Typically, an expression vector contains an "expression cassette,""which includes, in the 5'"to 3'"direction, a promoter, a coding sequence encoding the fusion protein operatively associated with the promoter, and, optionally, a termination sequence including a stop signal for RNA polymerase and a polyadenylation signal for polyadenylase.

Expression vectors can be designed for expression of polypeptides in prokaryotic or eukaryotic cells. For example, polypeptides can be expressed in bacterial cells such as *E. coli*, insect cells (e.g., in the baculovirus expression system), yeast cells, mammalian cells, or plant cells. Examples of vectors for expression in yeast *S. cerevisiae* include pYepSec1 (Baldari et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Baculovirus vectors available for expression of nucleic acids to produce proteins in cultured insect cells (e.g., Sf9 cells) include the pAc series (Smith et al., (1983) *Mol. Cell. Biol.* 3:2156-2165) and the pVL series (Lucklow, V. A., and Summers, M. d. (1989) *Virology* 170:31-39).

Additionally, the expression vector will generally include expression control sequences (e.g., transcription/translation control signals and polyadenylation signals), which are operably associated with the nucleic acid sequence encoding the fusion protein of the invention. It will be appreciated that a variety of promoter/enhancer elements can be used depending on the level and tissue-specific expression desired. The promoter can be constitutive or inducible (e.g., the metallothionein promoter or a hormone inducible promoter), depending on the pattern of expression desired. The promoter can be native or foreign and can be a natural or a synthetic sequence. By foreign, it is intended that the promoter is not found in the wild-type host into which the promoter is introduced. The promoter is chosen so that it will function in the target cell(s) of interest. Moreover, specific initiation signals are generally provided for efficient translation of inserted protein coding sequences. These translational control sequences, which can include the ATG initiation codon and adjacent sequences, can be of a variety of origins, both natural and synthetic. In embodiments of the invention wherein the expression vector comprises two open reading frames to be transcribed, the open reading frames can be operatively associated with separate promoters or with a single upstream promoter and one or more downstream internal ribosome entry site (IRES) sequences (e.g., the picornavirus EMC IRES sequence).

Examples of mammalian expression vectors include pCDM8 (Seed, (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40.

The invention further provides a host cell comprising (transiently or stably) a nucleic acid encoding a fusion protein of the invention. Suitable host cells are well-known in the art and include prokaryotic and eukaryotic cells. See e.g., Goeddel, *Gene Expression Technology*: Methods in Enzymology 185, Academic Press, San Diego, Calif. (1990). It is well-known that proteins can be expressed in bacterial cells such as *E. coli*, insect cells (e.g., the baculovirus expression system), yeast cells, plant cells or mammalian cells (e.g. human, rat, mouse, hamster, bovine, porcine, ovine, caprine, equine, feline, canine, lagomorph, simian and the like). The host cell can be a cultured cell such as a cell of a primary or immortalized cell line. The host cell can be a cell in a microorganism, animal or plant being used essentially as a bioreactor. In particular embodiments of the present invention, the host cell is an insect cell that allows for replication of expression vectors. For example, the host cell can be from *Spodoptera frugiperda*, such as the Sf9 or Sf21 cell lines, drosophila cell lines, or mosquito cell lines, e.g., *Aedes albopictus* derived cell lines. Use of insect cells for expression of heterologous proteins is well documented, as are methods of introducing nucleic acids, such as vectors, e.g., insect-cell compatible vectors (such as baculovirus vectors), into such cells and methods of maintaining such cells in culture. See, for example, Methods in Molecular Biology, ed. Richard, Humana Press, NJ (1995); O'Reilly et al., Baculovirus Expression Vectors, A Laboratory Manual, Oxford Univ. Press (1994); Samulski et al., *J. Vir.* 63:3822-8 (1989); Kajigaya et al., *Proc. Nat'l. Acad. Sci. USA* 88:4646-50 (1991); Ruffing et al., *J. Vir.* 66:6922-30 (1992); Kimbauer et al., *Vir.* 219:37-44 (1996); Zhao et al., *Vir.* 272:382-93 (2000); and U.S. Pat. No. 6,204,059 to Samulski et al. In particular embodiments of the present invention, the insect cell is an Sf9 cell.

Vectors can be introduced into prokaryotic or eukaryotic cells via conventional transformation or transfection techniques. As used herein, the terms "transformation""and "transfection""refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

In further embodiments of the present invention, the host cell can be stably transformed with the heterologous nucleic acid sequence encoding the fusion protein. "Stable transformation""as used herein generally refers to the integration of the heterologous nucleic acid sequences into the genome of the host cell in contrast to "transient transformation" wherein the heterologous nucleic acid sequence introduced into the host cell does not integrate into the genome of the host cell. The term "stable transformant""can further refer to stable maintenance of an episome (e.g. Epstein-Barr Virus (EBV)) in the cell.

When producing stably transformed cells, often only a small fraction of cells (in particular, mammalian cells) integrate a foreign nucleic acid into their genome. In order to identify and select these integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

The fusion protein can also be produced in a transgenic plant in which the isolated nucleic acid encoding the fusion protein is inserted into the nuclear or plastidic genome. Plant transformation is known as the art. See, in general, *Methods in Enzymology* Vol. 153 ("Recombinant DNA Part D") 1987, Wu and Grossman Eds., Academic Press and European Patent Application EP 693554.

Foreign nucleic acids can be introduced into plant cells or protoplasts by several methods. For example, nucleic acid can be mechanically transferred by microinjection directly into plant cells by use of micropipettes. Foreign nucleic acid can also be transferred into a plant cell by using polyethylene glycol which forms a precipitation complex with the genetic material that is taken up by the cell (Paszkowski et al. (1984) *EMBO J.* 3:2712-22). Foreign nucleic acid can be introduced into a plant cell by electroporation (Fromm et al. (1985) *Proc. Natl. Acad. Sci. USA* 82:5824). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells comprising the foreign nucleic acid can be accomplished using phenotypic markers.

Cauliflower mosaic virus (CaMV) can be used as a vector for introducing foreign nucleic acids into plant cells (Hohn et al. (1982) "Molecular Biology of Plant Tumors," Academic Press, New York, pp. 549-560; Howell, U.S. Pat. No. 4,407, 956). CaMV viral DNA genome is inserted into a parent bacterial plasmid creating a recombinant DNA molecule which can be propagated in bacteria. The recombinant plasmid can be further modified by introduction of the desired DNA sequence. The modified viral portion of the recombinant plasmid is then excised from the parent bacterial plasmid, and used to inoculate the plant cells or plants.

High velocity ballistic penetration by small particles can be used to introduce foreign nucleic acid into plant cells. Nucleic acid is disposed within the matrix of small beads or particles, or on the surface (Klein et al. (1987) *Nature* 327:70-73). Although typically only a single introduction of a new nucleic acid segment is required, this method also provides for multiple introductions.

A nucleic acid can be introduced into a plant cell by infection of a plant cell, an explant, a meristem or a seed with *Agrobacterium tumefaciens* transformed with the nucleic acid. Under appropriate conditions, the transformed plant cells are grown to form shoots, roots, and develop further into plants. The nucleic acids can be introduced into plant cells, for example, by means of the Ti plasmid of *Agrobacterium tumefaciens*. The Ti plasmid is transmitted to plant cells upon infection by *Agrobacterium tumefaciens*, and is stably integrated into the plant genome (Horsch et al., (1987) *Science* 227:1229-1231; Fraley et al. (1983) *Proc. Natl. Acad. Sci. USA* 80:4803).

The fusion protein can be expressed from the nucleic acid operably associated with other peptides or proteins, for example, operably associated with purification signals (such as poly His) or as a chimera with other proteins (e.g., cytokines).

5. Methods of Administering the Fusion Proteins, Flagellin Adjuvants, and Compositions of the Invention.

The present invention can be practiced for therapeutic and prophylactic purposes, in accordance with known techniques (see, e.g., PCT Application WO 2004/101737 to Pizzo et al.).

Generally, the present invention is practiced prophylactically to prevent infection by *Y. pestis* and/or to reduce and/or ameliorate the effects of infection by *Y. pestis*. In other embodiments, however, the methods of the invention are practiced to treat a subject that has already been infected by *Y. pestis*. Immunogenic compositions for use in the inventive methods are described below. Boosting dosages can further be administered over a time course of weeks, months or years. In chronic infection, initial high doses followed by boosting doses may be advantageous.

By the term "treat,""“treating""or "treatment of""(or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder. The term "treat,""“treats,""“treating," or "treatment of""and the like also include prophylactic treatment of the subject (e.g., to prevent the onset of infection or cancer). As used herein, the term "prevent,""“prevents,""or "prevention""(and grammatical equivalents thereof) are not meant to imply complete abolition of disease and encompasses any type of prophylactic treatment that reduces the incidence of the condition, delays the onset and/or progression of the condition, and/or reduces the symptoms associated with the condition. Thus, the term "treat,""“treating""or "treatment of" (or grammatically equivalent terms) refer to both prophylactic and therapeutic regimens.

The terms "vaccination""or "immunization""are well-understood in the art, and are used interchangeably herein unless otherwise indicated. For example, the terms vaccination or immunization can be understood to be a process that increases an organism's immune response to antigen and therefore to resist or overcome infection. In the case of the present invention, vaccination or immunization against *Y. pestis* increases the organism's immune response and resistance to *Y. pestis*.

As used herein, a "treatment effective amount""is an amount that is sufficient to treat (as defined herein) the subject.

An "active immune response""or "active immunity""is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both.""Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host.""Id.

A "protective""immune response or "protective""immunity as used herein indicates that the immune response confers some benefit to the subject in that it prevents or reduces the incidence and/or severity of disease. Alternatively, a protective immune response or protective immunity may be useful in the therapeutic treatment of existing disease.

The present invention can be practiced for both medical and veterinary purposes. Subjects to be treated by the methods of the invention include both avian and mammalian subjects, mammalian subjects including but not limited to humans, non-human primates (e.g., monkeys, apes, baboons, and chimpanzees), dogs, cats, rabbits, goats, horses, pigs, cattle, sheep, and the like (including both male and female subjects and subjects of all ages including infant, juvenile, adolescent and adult subjects). Subjects may be treated for any purpose, such as for eliciting a protective immune response; for eliciting the production of antibodies in that subject (typically an animal subject) which antibodies can be collected and used for other purposes such as diagnostic purposes or administering to other subjects to produce passive immunity therein, etc. In particular embodiments, the subject has or is considered at risk for *Y. pestis* infection.

In some embodiments the subjects are aged subjects, e.g., human subjects 50 or 60 years old or more, where other adjuvants such as alum are generally less effective.

Accordingly, in particular embodiments, the invention provides a method of inducing an immune response against *Y. pestis* in a subject (such as a mammalian subject, e.g., human or primate), the method comprising administering a fusion protein of the invention or a pharmaceutical composition thereof to the subject in an immunogenically effective amount. In representative embodiments, the method is practiced to protect a subject (such as a mammalian subject, e.g., human or primate) from the effects of *Yersinia pestis* infection, the method comprising administering a fusion protein of the invention or a pharmaceutical composition thereof to the subject in an amount effective to protect the subject from the effects of *Yersinia pestis* infection. Optionally, these methods are practiced by delivering the fusion protein or pharmaceutical composition to a mucosal surface (e.g., by intranasal or inhalation administration).

The invention further provides a method of inducing an immune response to *Y. pestis* in a subject (such as a mammalian subject, e.g., human or primate), the method comprising administering a flagellin adjuvant and a *Y. pestis* antigen, or a pharmaceutical composition(s) thereof, to the subject in an immunogenically effective amount. In representative embodiments, the method is practiced to protect a subject (such as a mammalian subject, e.g., human or primate) from the effects of *Y. pestis* infection, the method comprising administering a flagellin adjuvant and a *Y. pestis* antigen, or a pharmaceutical composition(s) thereof, to the subject in an amount effective to protect the subject from the effects of *Y. pestis* infection. Optionally, this method is practiced by delivering the fusion protein or pharmaceutical composition to a mucosal surface (e.g., by intranasal or inhalation administration). The flagellin adjuvant and *Y. pestis* antigen can be administered in the same or separate compositions. If administered as separate compositions, they can optionally be administered concurrently. As used herein, the term "concurrently""means sufficiently close in time to produce a combined effect (that is, concurrently can be simultaneously, or it can be two or more events occurring within a short time period [e.g., minutes or hours]"before or after each other).

Administration can be by any route known in the art. As non-limiting examples, the route of administration can be by inhalation (e.g., oral and/or nasal inhalation), oral, buccal (e.g., sublingual), rectal, vaginal, topical (including administration to the airways), intraocular, transdermal, by parenteral (e.g., intramuscular [including administration to skeletal, cardiac and/or diaphragm muscle], intravenous, subcutaneous, intradermal, intrapleural, intracerebral and intra-arterial, and intrathecal) routes, as well as direct tissue or organ injection, or by administration to the central nervous system (e.g., stereotactic administration to the brain).

In particular embodiments, administration is to a mucosal surface, e.g., by intranasal, inhalation, intra-tracheal, oral, rectal or vaginal administration, and the like. In general, mucosal administration refers to delivery to a mucosal surface such as a surface of the respiratory tract, gastrointestinal tract, urinary tract, reproductive tract, etc.

Methods of administration to the respiratory tract include but are not limited to transmucosal, intranasal, inhalation or intratracheal administration or administration to the lungs. Other methods of mucosal administration include oral, buccal (e.g., sub-lingual), intra-tracheal, rectal, vaginal and intra-ocular administration.

The protein(s) of the invention can be delivered per se or by delivering a nucleic acid intermediate that encodes the protein(s) and is expressed in the subject to produce the protein(s), such as described in U.S. Pat. No. 5,589,466 to Felgner et al.

Immunomodulatory compounds, such as immunomodulatory chemokines and cytokines (preferably, CTL inductive cytokines) can be co-administered to a subject. Cytokines may be administered by any method known in the art. Exogenous cytokines may be administered to the subject, or alternatively, a nucleotide sequence encoding a cytokine may be delivered to the subject using a suitable vector, and the cytokine produced in vivo. In particular embodiments, the cytokine is provided as fusion protein with the flagellin adjuvant and/or *Y. pestis* antigen. For example, a fusion protein comprising a flagellin adjuvant, a *Y. pestis* antigen, and an immunomodulatory cytokine (e.g., interferon-γ) can be administered. Alternatively, a fusion protein comprising the cytokine and the *Y. pestis* antigen or the flagellin adjuvant can be administered.

In addition to their use for prophylactic or therapeutic purposes, the fusion proteins and compositions of the present invention can be administered to subjects for the purpose of producing antibodies to a *Y. pestis* antigen, which antibodies are in turn useful for diagnostic or therapeutic/prophylactic purposes in human and animal subjects.

6. Pharmaceutical Compositions.

The invention further provides pharmaceutical compositions (e.g., immunogenic compositions) comprising a fusion protein of the invention in a pharmaceutically acceptable carrier. In particular embodiments, the pharmaceutical composition is formulated for mucosal delivery. By "pharmaceutically acceptable""it is meant a material that is not toxic or otherwise undesirable.

In representative embodiments, the fusion protein is present in the pharmaceutical composition in an "immunogenically effective""amount. An "immunogenically effective amount""is an amount that is sufficient to evoke an active immune response (i.e., cellular and/or humoral) in the subject to which the pharmaceutical composition is administered. Optionally, the dosage is sufficient to produce a protective immune response (prophylactic or therapeutic after onset of infection). The degree of protection conferred need not be complete or permanent, as long as the benefits of administering the pharmaceutical composition outweigh any disadvantages thereof. Immunogenically effective amounts depend on the protein, the manner of administration, the stage and severity of the disease being treated, the weight and general state of health of the subject, and the judgment of the prescribing physician.

Dosages of pharmaceutically active compounds can be determined by methods known in the art, see, e.g., *Remington's Pharmaceutical Sciences* (Maack Publishing Co., Easton, Pa.). In particular embodiments, the dosage of the fusion proteins of the present invention ranges from about 0.1, 0.5, 1, 10, 25, 250, 100, 150 or 250 μg to about 300, 500, 1000, 2500, 5000 or 10,000 μg of fusion protein for a typical (e.g. 70 kg) subject. In particular embodiments, dosages are in the range of about 50 to 2000 μg, about 100 to 1500 μg, or about 250 to 1000 μg for a typical subject. The initial dose can be followed by boosting dosages over weeks, months or years of from about 1 µg to 250, 500 or 1000 µg depending on the subject's response to the initial dosage.

The invention also provides a pharmaceutical composition comprising: (a) a flagellin adjuvant; and (b) a *Yersinia pestis* antigen. In particular embodiments, the pharmaceutical composition is formulated for mucosal administration. As described in more detail herein, the *Y. pestis* antigen can be a *Y. pestis* F1 antigen, a *Y. pestis* V antigen, or a fusion peptide thereof. Optionally, the *Y. pestis* antigen is coupled to the flagellin adjuvant, i.e., is in the form of a fusion protein with the flagellin antigen. According to this embodiment, the composition can further comprise one or more additional *Y. pestis* antigens that are not coupled to the flagellin adjuvant (i.e., is not part of a fusion protein with the flagellin adjuvant).

Optionally, the *Y. pestis* antigen is present in an immunogenically effective amount, as defined herein. Further, in some embodiments, the flagellin adjuvant is present in an "adjuvant effective amount.""An "adjuvant effective amount""is an amount of the flagellin adjuvant that is sufficient to enhance or stimulate the active immune response (cellular and/or humoral) mounted by the host against the *Y. pestis* antigen, optionally an active mucosal immune response. In particular embodiments, the active immune response (e.g., a mucosal immune response) by the host is enhanced by at least about 2, 3, 4, 5, 10, 15, 20, 30, 40, 50, 60, 75, 100, 150, 500, 1000-fold or more. In other embodiments, an "adjuvant effective amount""is an amount of the flagellin adjuvant that reduces the amount of antigen required to achieve a specified level of immunity (cellular and/or humoral), optionally mucosal immunity, for example, a reduction of at least about 15%, 25%, 35%, 50%, 65%, 75%, 80%, 85%, 90%, 95%, 98% or more in the amount of antigen. As a further option, an "adjuvant effective amount""can refer to an amount of the flagellin adjuvant that accelerates the induction of the immune response in the host and/or reduces the need for booster immunizations to achieve protection. As yet another alternative, an "adjuvant effective amount""can be an amount that prolongs the time period over which an immune response, optionally protective immune response, is sustained (e.g., by at least about a 2-fold, 3-fold, 5-fold, 10-fold, 20-fold longer time period or more).

Dosages of the flagellin adjuvant and *Y. pestis* antigen (if not in the form of a fusion protein) can be determined by those skilled in the art. In particular embodiments, dosages of the flagellin adjuvant are in the range from about 0.1, 0.5, 1, 10, 25, 50, 100 or 150 µg to about 200, 250, 300, 500, 1000, or 2500 µg for a typical (e.g., 70 kg) subject. In particular embodiments, dosages are from about 10 to 1000 µg, or from about 50 to 500 µg, or from about 150 to 300 µg for a typical subject. Suitable dosages of the *Y. pestis* antigen can range from about 0.1, 0.5, 1, 10, 25, 50, 100 or 150 µg to about 200, 300, 500, 1000, 1500, 2000, 2500 or 5000 µg for a typical (e.g. 70 kg) subject. In particular embodiments, the dosage of the *Y. pestis* antigen is from about 50 to 2000 µg, from about 150 to about 1500 µg, or from about 300 to about 1000 µg for a typical subject. The initial dose can be followed by boosting dosages over weeks, months or years of from about 1 µg to about 1000 µg depending on the subject's response to the initial dosage.

The pharmaceutical compositions of the invention can optionally comprise other medicinal agents, pharmaceutical agents, stabilizing agents, buffers, carriers, diluents, salts, tonicity adjusting agents, wetting agents, and the like, for example, sodium acetate, sodium lactate, sodium chloride, potassium chloride, calcium chloride, sorbitan monolaurate, triethanolamine oleate, etc.

For injection, the carrier will typically be a liquid. For other methods of administration, the carrier may be either solid or liquid. For inhalation administration, the carrier will be respirable, and is typically in a solid or liquid particulate form.

While adjuvants beyond flagellin are generally not required, the composition can optionally comprise an additional adjuvant, such as complete or incomplete Freund's adjuvant, aluminum phosphate, aluminum hydroxide, alum, cytokines, TLR ligands, and the like.

The concentration of the proteins in the pharmaceutical compositions can vary widely, e.g., from less than about 0.01% or 0.1% up to at least about 2% to as much as 20% to 50% or more by weight, and will be selected primarily by fluid volumes, viscosities, etc., in accordance with the particular mode of administration selected.

The proteins can be formulated for administration in a pharmaceutical carrier in accordance with known techniques. See, e.g., Remington, *The Science And Practice of Pharmacy* ($9^{th}$ Ed. 1995). In the manufacture of a pharmaceutical composition according to the invention, the protein(s) (including physiologically acceptable salts thereof) is typically admixed with, inter alia, an acceptable carrier. The carrier can be a solid or a liquid, or both, and is optionally formulated with the compound as a unit-dose formulation, for example, a tablet. A variety of pharmaceutically acceptable aqueous carriers can be used, e.g., water, buffered water, 0.9% saline, 0.3% glycine, hyaluronic acid, pyrogen-free water, pyrogen-free phosphate-buffered saline solution, bacteriostatic water, or Cremophor EL[R]"(BASF, Parsippany, N.J.), and the like. These compositions can be sterilized by conventional techniques. One or more proteins can be incorporated in the formulations of the invention, which can be prepared by any of the well-known techniques of pharmacy.

The pharmaceutical compositions can be packaged for use as is, or lyophilized, the lyophilized preparation generally being combined with a sterile aqueous solution prior to administration. The compositions can further be packaged in unit/dose or multi-dose containers, for example, in sealed ampoules and vials.

The pharmaceutical compositions can be formulated for administration by any method known in the art according to conventional techniques of pharmacy. For example, the compositions can be formulated to be administered intranasally, by inhalation (e.g., oral inhalation), orally, buccally (e.g., sublingually), rectally, vaginally, topically, intrathecally, intraocularly, transdermally, by parenteral administration (e.g., intramuscular [including administration to skeletal, cardiac and/or diaphragm muscle], intravenous, subcutaneous, intradermal, intrapleural, intracerebral and intra-arterial, intrathecal), topically (e.g., to both skin and mucosal surfaces, including airway surfaces), as well as direct tissue or organ injection, and by administration to the central nervous system (e.g., stereotactic administration to the brain).

In particular embodiments, the pharmaceutical composition is administered to a mucosal surface, e.g., by intranasal, inhalation, intratracheal, oral, rectal or vaginal administration, and the like.

For intranasal or inhalation administration, the pharmaceutical composition can be formulated as an aerosol (this term including both liquid and dry powder aerosols). For example, the pharmaceutical composition can be provided in a finely divided form along with a surfactant and propellant. Typical percentages of the composition are 0.01-20% by weight, preferably 1-10%. The surfactant is generally nontoxic and soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. The balance of the composition is ordinarily propellant. A carrier can also be included, if desired, as with lecithin for intranasal delivery. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles can likewise be produced with any solid particulate medicament aerosol generator, by techniques known in the pharmaceutical art. Intranasal administration can also be by droplet administration to a nasal surface.

Injectable formulations can be prepared in conventional forms, either as liquid solutions or suspensions, solid forms suitable for solution or suspension in liquid prior to injection, or as emulsions. Alternatively, one can administer the pharmaceutical composition in a local rather than systemic manner, for example, in a depot or sustained-release formulation.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is pharmaceutically acceptable, can be included in sufficient quantity to emulsify the composition in an aqueous carrier. One such useful emulsifying agent is phosphatidyl choline.

Pharmaceutical compositions suitable for oral administration can be presented in discrete units, such as capsules, cachets, lozenges, or tables, as a powder or granules; as a solution or a suspension in an aqueous or non-aqueous liquid; or as an oil-in-water or water-in-oil emulsion. Oral delivery can be performed by complexing a compound(s) of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the compound(s) and a suitable carrier (which may contain one or more accessory ingredients as noted above). In general, the pharmaceutical compositions are prepared by uniformly and intimately admixing the compound(s) with a liquid or finely divided solid carrier, or both, and then, if necessary, shaping the resulting mixture. For example, a tablet can be prepared by compressing or molding a powder or granules containing the compound(s), optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the compound(s) in a flavored base, usually sucrose and acacia or tragacanth; and pastilles comprising the compound(s) in an inert base such as gelatin and glycerin or sucrose and acacia.

Pharmaceutical compositions of this invention suitable for parenteral administration can comprise sterile aqueous and non-aqueous injection solutions of the compounds of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical compositions suitable for rectal administration are preferably presented as unit dose suppositories. These can be prepared by admixing the compound(s) with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharmaceutical Research* 3:318 (1986)) and typically take the form of an optionally buffered aqueous solution of the compound(s). Suitable formulations can comprise citrate or bis\tris buffer (pH 6) or ethanol/water and can contain from 0.1 to 0.2M active ingredient.

Further, the compound(s) can be formulated as a liposomal formulations. The technology for forming liposomal suspensions is well known in the art. When the compound(s) or salt thereof is an aqueous-soluble salt, using conventional liposome technology, the same can be incorporated into lipid vesicles. In such an instance, due to the water solubility of the compound(s) or salt, the compound(s) or salt will be substantially entrained within the hydrophilic center or core of the liposomes. The lipid layer employed can be of any conventional composition and can either contain cholesterol or can be cholesterol-free. When the compound(s) or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations can be lyophilized to produce a lyophilizate which can be reconstituted with a pharmaceutically acceptable carrier, such as water, to regenerate a liposomal suspension.

Having described the present invention, the same will be explained in greater detail in the following examples, which are included herein for illustration purposes only, and which are not intended to be limiting to the invention. Abbreviations used herein are as follows: GM-CSF, granulocyte-macrophage colony stimulating factor; IL, interleukin; i.n., intranasal; i.t., intra-tracheal; NK, natural killer cell; NO, nitric oxide; s.c., subcutaneous; TLR, toll like receptor; TGF-β; transforming growth factor beta.

EXAMPLE 1

Cancer Antigens and Vaccines thereof

Effect of flagellin on innate immunity in the mouse lung. Non-surgical intratracheal (i.t.) instillation of 1 μg of flagellin is sufficient to induce maximal production of TNFα"after approximately 4 hr (FIG. 1). By 12-24 hr, cytokine levels in broncheoalveolar lavage fluid return to baseline levels. Note that a mutant flagellin that does not bind to TLR5 and thus lacks signaling activity, did not induce cytokine production. In addition to TNFα, several other cytokines including IL-6, G-CSF, and the chemokines, MIP-2 and KC were induced to relatively high levels. The increase in cytokine expression is followed by the transient infiltration of neutrophils (maximal at 12-24 hr). It is important to emphasize that the innate immune response initiated by flagellin does not result in severe tissue damaging inflammation. The induced inflammatory response is relatively moderate and acute in nature. These findings, in conjunction with those of other investigators, establish the in vivo potency of flagellin as an activator of innate immunity.

Figure 5:
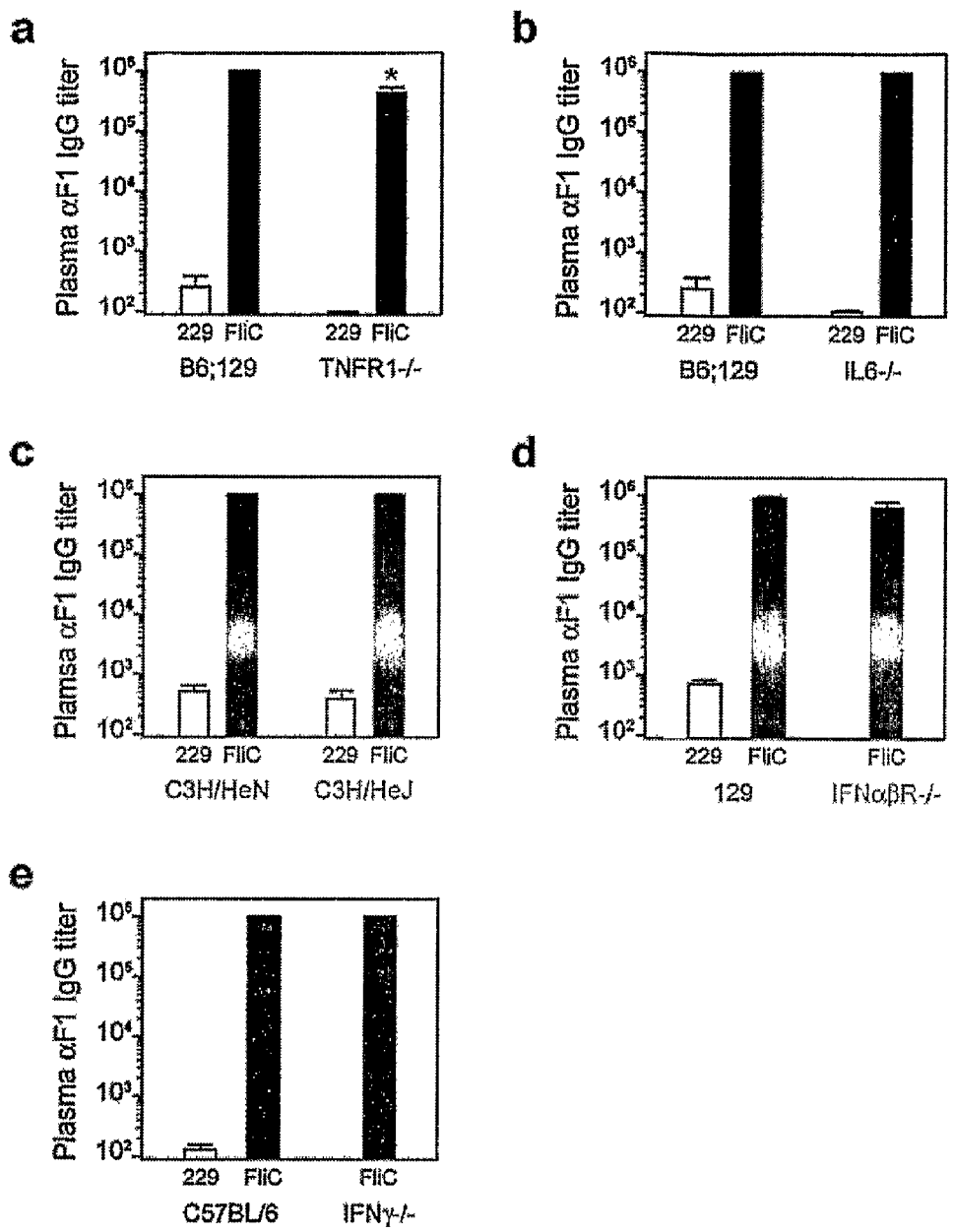
FIGS. 5a to 5e depict the requirements for the adjuvant effects of flagellin. $TNFR^{-/-}$"(panel a) or $IL6^{-/-}$"(panel b) and wild-type B6; 129 control mice were immunized i.t. with 10 µg F1 antigen+1 µg flagellin (FliC) or mutant flagellin (229). * indicates $TNFR^{-/-}$"titers are statistically less than B6; 129 control ($p<0.001$). C3H/HeJ (Tlr4 P712H mutant) and wild-type C3H/HeN mice were immunized with 10 µg F1+1 µg FliC or 229 (panel c). $IFN\alpha/\beta R^{-/-}$"(panel d) and $IFN\gamma^{-/-}$"(panel e) mice and corresponding wild-type controls were immunized i.n. with 10 µg F1+1 µg FliC or 229. Seven female mice were used in each immunization group. Mice were boosted in the same manner at 4 weeks and plasma was collected 2 weeks later for analysis of anti-F1 IgG titers by ELISA. Bars represent mean antibody titers±s.e.m.
Figure 6:
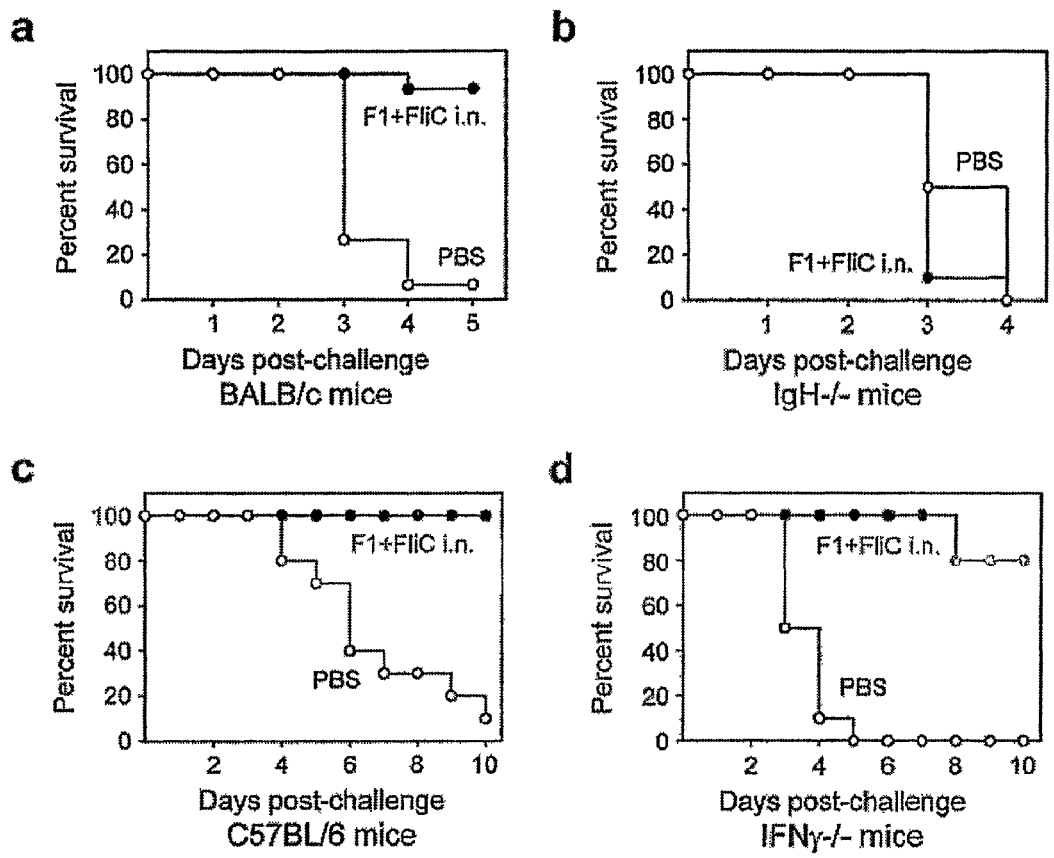
FIGS. 6a 6d show that flagellin promotes a protective response for intranasal infection with Yersinia pestis CO92. Groups of 15 female BALB/c mice (panel a) were immunized i.n. with 10 µg F1 antigen+1 µg flagellin (FliC) or PBS alone and boosted in an identical manner at 4 weeks. Plasma was collected 2 weeks post-boost for analysis of antibody titers by ELISA (mean anti-F1 titer=$9.4\times10^5$). One week later mice were challenged i.n. with a dose of Y. pestis CO92 equivalent to $100\times LD_{50}$. Mice were monitored for 30d post-challenge. Groups of 10 antibody-deficient $IgH^{-/-}$"mice (panel b) were immunized i.n. with 10 µg F1+1 µg FliC or PBS alone and boosted in an identical manner at 4 weeks. Mice were challenged two weeks later i.n. with a dose of Y. pestis equivalent to $155\times LD_{50}$. Groups of 10 wild-type C57BL/6 mice (panel c) and female $IFN\gamma^{-/-}$"mice (panel d) were immunized and boosted i.n. with 10 µg F1+1 µg FliC. Plasma was collected 2 weeks post-boost for analysis of antibody titers by ELISA (anti-F1 titer$\geq 1\times10^6$). One week later mice were challenged i.n. with a dose of Y. pestis equivalent to $150\times LD_{50}$ and monitored for 16d post-challenge.

Adjuvant effect of flagellin in the mouse lung. In addition to analyzing the innate response induced by flagellin, the effects of flagellin on the antibody response were examined. BALB/c mice were immunized with 10 μg F1 antigen with 1 μg flagellin or an inactive flagellin mutant protein by non-surgical intra-tracheal (i.t.) or intra-nasal (i.n.) instillation. Four weeks later, the mice were boosted with the same regimens and then serum levels of anti-F1 IgG were determined two weeks later. Flagellin, but not the inactive mutant, exhibited extraordinarily potent adjuvant activity as measured by serum anti-F1 IgG levels. In animals immunized i.t., the antibody titers ranged from 20,000 to greater than 100,000, and from 90,000 to greater than 300,000 in the case of animals immunized i.n. The results for i.n. immunization are presented in Table 1. Analysis of the cytokine requirements for this response using knockout mice indicate that neither IL-6, IL-12, nor TNF-α"are required for the adjuvant effect of flagellin (FIG. 5). Furthermore, the maximal adjuvant effect of flagellin is achieved with a dose of flagellin (1 μg) that is 5-10×"less than required for the maximal induction of the innate immune response in the respiratory tract of mice. Thus maximal adjuvant activity is achieved with a dose of flagellin that produces limited inflammation.

TABLE 1

I.n. immunization with *Y. pestis* F1 antigen and wild-type flagellin results in a strong anti-F1 IgG response. Mice were given two immunizations with 10 μg F1 antigen and 1 μg wild-type or mutant flagellin. Serum anti-F1 IgG titers were measured by ELISA.

| Flagellin | Total IgG Titer |
|---|---|
| Inactive mutant (7 mice) | <100 |
| wild-type mouse 1 | >300,000 |
| mouse 2 | >300,000 |
| mouse 3 | >300,000 |
| mouse 4 | 90,000 |
| mouse 5 | >300,000 |
| mouse 6 | 300,000 |

EXAMPLE 2

Flagellin as an Adjuvant to Produce an Antigen-Specific Breast Cancer Response Treatment of breast tumor in vivo. BALB/c mice were immunized with the Fra-1 antigen, an antigen that is over-expressed by many breast tumors, and either flagellin or an inactive form of flagellin. The mice were boosted once prior to subcutaneous injection of D2F2 cells, a breast cancer tumor. The mice were monitored for the growth of tumors and the tumor volumes were determined. Data are shown in FIG. 2. The open circles represent the mice given the Fra-1 antigen and the inactive form of flagellin. The closed circles represent the mice given Fra-1 antigen and the active form of flagellin. As can readily be seen, flagellin+Fra-1 antigen had a significant effect on the growth of the tumor.

Evaluation of whether flagellin can promote a protective immune response against D2F2 breast cancer cells in a mouse model. The ability of flagellin to promote a protective state of immunity against D2F2 breast cancer cells is evaluated using as an antigen, Fra-1, a protein that is over-expressed by these cancer cells These experiments involve immunization and then challenge with D2F2 cells as well as challenge followed by immunization. In addition, the nature of the induced effectors-antibodies vs. cytolytic T cells and/or NK cells is determined.

A. Preparation of purified recombinant Fra-1 antigen. The pET22 expression vector encoding the cDNA encoding murine Fra-1 (kindly provided by Dr. Rong Xiang, The Scripps Research Institute) is used to express the Fra-1 protein in Rosetta-gami-pLysS bacteria. The protein is purified using the Talon affinity resin (via recognition of the His-tag on the Fra-1) and contaminating endotoxin is removed by passage of the purified protein over a DETOXI-GEL®"column (McDermott et al. (2000) *Infect. Immun.* 68:5525-5529). Using this procedure, mg amounts of several proteins have been obtained previously (e.g., flagellin, F1 antigen, and IRAK-4 [a eukaryotic protein]).

B. Evaluation of whether flagellin promotes protective immunity against D2F2 breast cancer cells in BALB/c mice immunized with Fra-1 antigen and flagellin. Groups of 7 mice are immunized with 10 μg Fra-1 protein with or without 1 μg flagellin or mutant flagellin 229 intra-peritoneally (i.p.) or intramuscularly (i.m.). Two weeks later, the mice are boosted and then challenged with 1×106 D2F2 cells (given subcutaneously (s.c.)). Tumor mass and the survival of the mice is followed over a period of approximately 3 months. In the absence of immunity, approximately 50% of the mice succumb within 4 weeks after challenge. The s.c. tumors are measured for width and length so that tumor volume can be calculated. If a significant effect of flagellin is observed, the dose of flagellin that produces the maximal response is determined. Once the optimal dose of flagellin is established, it is determined if flagellin can promote the clearance of an existing tumor. Groups of 7 mice are challenged with D2F2 cells by s.c. injection and then immunized with Fra-1 with or without flagellin at the time of challenge or 1, 3, 7, and 21 days later. In each case, the mice are boosted after 2 weeks. Tumor mass and survival of the mice are determined.

C. Identification of the potential effectors in the flagellin-promoted response against Fra-1-expressing D2F2 cells. To identify the induced effectors in the flagellin-promoted response, the level of circulating anti-Fra-1 antibodies as well as the relative numbers of CD8+"cytolytic T cells (CTL) and NK cells are determined. BALB/c mice are immunized with Fra-1 and flagellin or mutant flagellin according to the protocol presented above.

1. Anti-Fra-1 antibodies. Two weeks after challenge with D2F2 cells, the mice are euthanized and serum samples are taken for analysis of circulating anti-Fra-1 antibodies by ELISA. Using appropriate anti-isotypic antibodies, the levels of circulating total IgG and IgM as well as IgG1 and IgG2a sub-isotypes are assessed.

2. Anti-Fra-1 specific CD8+"CTL. Anti-Fra-1 specific CD8+"CTL are determined by isolating splenocytes and assessing their cytolytic activity in a standard $^{51}$Cr-release assay. The lysis mediated by CD8+"CTL should be blocked by an anti-MHC class I antibody. Therefore, cell samples are analyzed in the presence and absence of this antibody. By varying the ratio of effectors-to-targets, a relative estimate of the increase in CD8+"CTL in mice immunized with Fra-1 and flagellin or mutant flagellin is obtained. The numbers of activated CD8+"CTL can also be determined using an ELISPOT assay for interferon-γ"(IFN-γ) production. Using anti-CD8 MACS MicroBeads (Miltenyl Biotech), CD8+"splenocytes from immunized mice are isolated and the cells incubated for 24 h with irradiated D2F2 cells. The cells are analyzed by ELISPOT assay for IFN-γ"production. If sufficient numbers of cells are present, intracellular cytokine staining (ICS) is used as a second method.

3. NK cells. The relative numbers of activated NK cells are assessed in a $^{51}$Cr-release assay using YAC-1 cells as targets. Splenocytes are obtained from immunized and D2F2 challenged mice and assessed for cytolytic activity against YAC-1 cells. Since the expression of DX5 is associated with NK cells, the expression of this marker by flow cytometry is measured using a commercially available PE-labeled antibody. A stimulatory effect of flagellin on the expansion of NK cells should be associated with an increase in DX5 expression.

The efficacy of a recombinant flagellin protein containing Fra-1 epitopes in the protective response against D2F2 breast cancer cells. It is further determined if flagellin can serve as a vaccine vector and adjuvant. If this is the case, recombinant flagellin proteins encoding a number of epitopes from different tumor antigens are generated.

The available evidence indicates that human breast cancers exhibit substantial heterogeneity in the tumor-specific antigens that they express. For example, MAGE-3 is expressed in approximately 14% of breast cancers, whereas Her2/neu is expressed in 40%, NY-BR-62 in 60%, and NY-BR-85 in approximately 90% (Scanlan and Jäger (2001) *Breast Cancer Res.* 3:95-98). It is determined if a recombinant flagellin protein containing full-length Fra-1 antigen can function in the same manner as the two proteins.

If this is the case, then the epitopes within Fra-1 that are involved in inducing a protective response are mapped. It would be a straightforward effort to do the same thing with other major breast cancer antigen targets. A flagellin protein expressing epitopes from a range of target antigens can be generated. Alternatively, a cocktail of flagellin proteins can be used—each flagellin expressing a subset of target epitopes. Furthermore, by introducing foreign epitopes are introduced into the hypervariable region of the protein—a region that is not involved in the interaction of flagellin with TLR5 (Donnelly and Steiner (2002) *J. Biol. Chem.* 277:40456-40461; Smith et al. (2003) *Nat. Immunol.* 4:1247-1253; Murthy et al. (2004) *J. Biol. Chem.* 279:5667-5675), it is unlikely that the biologic activities of flagellin are affected in any significant manner.

Generation of a flagellin/Fra-1 chimera. The full sequence for Fra-1 is inserted into the hypervariable region of flagellin and the resultant construct is cloned into the pET22a expression vector and the protein is expressed in Rosetta-gami-pLysS bacteria. Endotoxin is removed using a DETOXI-GEL®"column. The biologic activity of the chimeric protein is assessed using TNFα"production by RAW264.7 cells. The chimera is titrated and its potency compared with wild-type flagellin.

Mapping of Fra-1 epitopes required for protection against D2F2 cells. The ability of the chimera to protect BALB/c mice against a challenge with D2F2 cells is evaluated. If the chimera induces protective immunity, overlapping truncations of the Fra-1 sequence are generated and tested for efficacy in the context of the flagellin. To reduce the number of constructs, three overlapping fragments covering the entire sequence of Fra-1 are prepared. If one of these truncations is active, additional truncations are generated to define the minimal sequence(s) that is required for protection. If none of the three truncations is functional by itself, these are tested in pairs to determine if the required sequences are in different parts of the protein. Using this approach, the minimal required sequences can be defined.

EXAMPLE 3

Flagellin is an Effective Mucosal Adjuvant for Immunization Against Lethal Respiratory Challenge with *Yersinia pestis*

Methods:

Plasmids and cell culture. The coding sequence for the F1 antigen of *Yersinia pestis*, caf1, (plasmid containing the entire caf operon kindly provided by Dr. J. B. Bliska, State University of New York, Stony Brook) was subcloned into the NdeI and XhoI sites of the pET29a expression vector from Novagen (EMD Biosciences, Inc., Madison, Wis.). The recombinant F1/V fusion construct (Heat et al. (1998) *Vaccine* 16:1131-1137) (provided by Drs. G. Andrews and P. Worsham, USAMRIID) was sequenced and subcloned into pET16b. Sequencing revealed the absence of 21 amino acids corresponding to the signal sequence of F1.

Reagents and antibodies. Purified, recombinant His-tagged flagellin from *Salmonella enteritidis* was prepared as described previously (Honko and Mizel (2004) *Infect. Immun.* 72:6676-6679; McDermott et al. (2000) *Infect. Immun.* 68:5525-5529). The 229 mutant flagellin, as well as the F1 and F1/V antigens were purified in an identical manner. Endotoxin levels were ≦1 pg/μg as detected by the QCL-1000®"Chromogenic LAL Test Kit from the Cambrex Corporation (East Rutherford, N.J.). TNF-α"was detected using the BD OptEIA ELISA kit (mono/mono) per the manufacturers instructions (BD Biosciences). An anti-F1 mouse monoclonal IgG1, clone YPF19 obtained from Research Diagnostics, Inc. (Flanders, N.J.), was used as a control in the anti-F1 ELISA. Goat anti-mouse IgG-HRP was purchased from SouthernBiotech (Birmingham, Ala.). Goat anti-monkey IgG-HRP was purchased from Research Diagnostics, Inc. (Flanders, N.J.).

Mice. Female BALB/cAnNCr mice were purchased from the Frederick Cancer Research and Development Center (Frederick, Md.). Female IL-6-/-"mice (B6; 129S2-Il6/J), TNFR1 mice (tm1Kopf-/-"B6; 129S-Tnfrsf1a Tnfrsf1b/J), IFNγ"(tm1Imx tm1 Imx-/- B6.129S7-Ifngtm1Ts/J) and control mice (C57BL/6J, B6; 129SF2/J and 129/SvJ) were purchased from The Jackson Laboratory (Bar Harbor, Me.). IFNα/βR-/-"mice were provided by Dr. C. Schindler, Columbia University, New York (Müller et al. (1994) *Science* 264:1918-1921). Mice were maintained in a specific-pathogen free facility and all research complied with federal and institutional guidelines set forth by the Wake Forest University Animal Care and Use Committee.

Nonsurgical intratracheal and intranasal immunization of mice. For intratracheal immunization, mice were anesthetized with Avertin (2,2,2-tribromoethanol, Sigma; tert-amyl alcohol, Fisher) by intraperitoneal injection and suspended from a length of wire by their front incisors. Using a sterile gel-loading tip inserted gently into the trachea, 10 μg F1 antigen and the indicated amount of flagellin or the flagellin mutant 229 was administered in a total of 50 μL pyrogen-free PBS. For intranasal immunization, small volumes (9-12 μL total) containing antigen and adjuvant in PBS were administered to the nostrils of anesthetized mice. Mice were boosted at 4 weeks and plasma collected 2-3 weeks post-boost for analysis of antibody titers.

Figure 3:
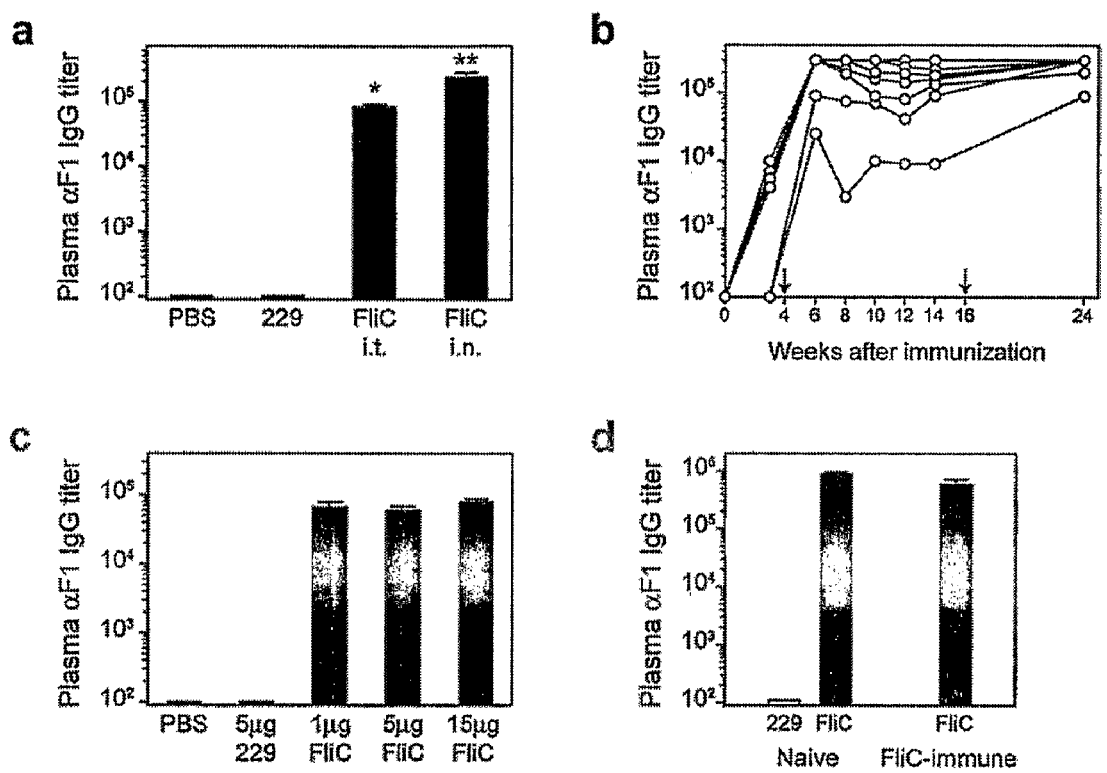
FIGS. 3a to 3d show that immunization with flagellin and the F1 antigen of Yersinia pestis results in substantial anti-F1 antibody production. (Panel a) Female BALB/c mice were immunized intratracheally (i.t.) or intranasally (i.n.) with 10 µg F1+1 µg flagellin (FliC). Control animals were immunized i.t. with 10 µg F1 alone or with 1 µg of the 229 mutant flagellin. Mice were boosted in an identical manner at 4 weeks and plasma was collected 2 weeks later for analysis by ELISA. Numbers within the bars indicate ratio of IgG1/IgG2a isotypes. * indicates statistical significance over controls and ** indicates i.n. titers are statistically greater than i.t. ($p<0.007$). (Panel b) Anti-F1 antibody titers from mice immunized i.n. with 10 µg F1+1 µg flagellin. Each line represents one mouse and arrows indicate booster immunizations. (Panel c) Female BALB/c mice were immunized i.t. with 10 µg F1 and increasing amounts of FliC or 5 µg of 229 and boosted at 4 weeks. Plasma anti-F1 IgG titers were determined 2 weeks post-boost. (Panel d) A group of female BALB/c mice was immunized i.n. with 5 µg of flagellin alone and boosted in an identical manner at 4 weeks. Anti-FliC antibody titers were determined 2 weeks later (mean anti-FliC titer=$8.5\times10^5$) and flagellin-immune mice were then immunized and boosted with 10 µg F1+1 µg FliC i.n. Two weeks post-boost, anti-F1 titers were determined and compared to titers of flagellin-naive animals immunized with 10 µg F1+1 µg FliC or 229. Bars represent mean antibody titers±s.e.m. Seven female BALB/c mice were used per immunization group.

Immunization of monkeys. Fifteen healthy adult female cynomolgus monkeys (*Macaca fascicularis*) were maintained in accordance with federal and institutional guidelines set forth by the Wake Forest University Animal Care and Use Committee. Animals were anesthetized with 7-10 mg/kg ketamine intramuscularly for immunizations and blood collection. For intranasal immunization, 150 μg F1/V fusion protein and 50 μg flagellin were delivered dropwise (100 μL/nostril) to animals in a recumbent position. Intramuscular immunizations were administered into the quadriceps in a volume of 1 mL. Control animals received PBS intranasally and intramuscularly.

Analysis of plasma antibody titers by enzyme-linked immunosorbant assay (ELISA). Heparinized tubes (StatSpin; Fisher Scientific) or BD Vacutainer PST tubes were used for plasma collection. Plasma was then aliquoted and frozen at −70°"C. until analysis. ELISA plates were coated with 100 μL of antigen at 10 μg/mL in sterile PBS overnight at 4°"C. and blocked with 10% FCS in PBS. Duplicate or triplicate plasma dilutions were added and the plate was incubated overnight at 4°"C., followed by secondary anti-Ig antibodies for 2 h at room temperature. Peroxidase activity was detected with 3,3',5,5'-Tetramethylbenzidine (TMB) Liquid Substrate System (Sigma-Aldrich) and stopped with 2M $H_2SO_4$. End-point dilution titers were defined as the inverse of the highest dilution that resulted in an absorbance value $(OD_{450})>0.1$ over that of naive plasma.

Respiratory challenge with *Yersinia pestis* CO92. The Centers for Disease Control (CDC) Division of Vector-Borne Infectious Diseases (Fort Collins, Colo.) provided a stock culture of *Yersinia pestis* CO92 biovar orientalis, a strain isolated from a fatal case of human primary pneumonic plague (Doll et al. (1994) *Am. J. Trop. Med. Hyg.* 51: 109-114). Heart infusion broth was inoculated with a single colony from a subculture plate and grown at 28°"C. to an approximate density of $1\times10^9$ colony forming units (cfu)/mL. Mice were challenged intranasally with 10 μL of culture diluted in PBS to $\sim1.8\times10^7$ cfu/mL, a dose equivalent to 150×"lethal dose 50% (LD50) of $1.2\times10^4$ cfu (data not shown). Actual cfu/mL values were determined by plating serial dilutions onto tryptose blood agar plates. Survival was monitored for 14-30 days post challenge. All experiments were conducted according to CDC approved standard operating procedures for the BSL3 and ABSL3 facility at the Infectious Disease Unit at Virginia Tech (CDC approval #C20031120-0016).

Statistical analysis. Data are represented as individual values with means and standard error. The F test for equality of variance and Student's one-sided t-test were used to assign statistical significance at $p<0.05$ or $p<0.01$. SigmaStat3.1 (Systat Software, Inc., Richmond, Calif.) was used to determine $LD_{50}$ values by nonlinear regression.

Results:

Immunization with flagellin promotes a potent adaptive response to the F1 antigen of *Yersinia pestis*. To determine the ability of flagellin to promote a humoral immune response against the F1 antigen of *Y. pestis*, BALB/c mice were immunized with 10 μg F1 antigen and 1 μg recombinant flagellin (FliC) intratracheally (i.t.) or intranasally (i.n.). Control animals were immunized with F1 antigen in PBS, or F1 and a mutant form of flagellin, designated 229. Four weeks later, mice were boosted in an identical manner and plasma was collected for analysis of circulating antibody titers at various times post-boost. No F1-specific IgG was detected in the groups of control mice. However, a vaccine containing F1 and flagellin stimulated a dramatic increase in total IgG titers (FIG. 3, panel a), with high levels of F1-specific IgG1 and IgG2a. The mean ratio of IgG1 to IgG2a (indicated within the bars) ranged from 30-170 when flagellin and F1 were administered i.t. and was approximately 3 when given i.n. Although i.n. and i.t. immunization resulted in mixed Th responses, the bias towards an apparent Th2 response was more evident following intratracheal immunization. It is important to note that flagellin did not promote significant F1-specific IgE production. Mice immunized with F1 and flagellin exhibited sustained titers of anti-F1 IgG after two immunizations (FIG. 3, panel b). A tertiary immunization at 16 weeks improved the antibody response in the two mice that had lower initial titers.

In a previous study, it was demonstrated that the innate response to flagellin in the lung was maximal with doses of flagellin in the range of 5-15 μg (Honko and Mizel (2004) *Infect. Immun.* 72:6676-6679). To determine if there was a linear relationship between the magnitude of the cytokine response and the antibody response promoted by flagellin, BALB/c mice were immunized with F1 antigen and 1 μg, 5 μg and 15 μg of flagellin (FIG. 3, panel c). Anti-F1 IgG titers were not significantly different at these doses, indicating that the adjuvant effect is maximal at 1 μg flagellin. However, we noticed a trend towards a greater IgG1/IgG2a ratio with increasing doses of flagellin. Thus it appears that a maximal adaptive response may not require a maximal innate response.

Pre-existing immunity to flagellin is an obvious concern when considering its use as an adjuvant. Therefore, we evaluated the effectiveness of immunization with flagellin and F1 in the presence of high titers of anti-flagellin antibodies. Female BALB/c mice were immunized and boosted with 5 μg flagellin i.n. and anti-flagellin antibody titers were determined. Flagellin-specific IgG titers were below the level of detection prior to immunization, and increased significantly with a mean anti-FliC IgG titer of $8.5 \times 10^5$. These mice were then immunized and boosted with 10 µg F1 and 1 µg FliC i.n. Two weeks post-boost, anti-F1 IgG titers were similar between naive and FliC-immune mice (FIG. 3, panel d), indicating that circulating anti-flagellin antibodies did not positively or negatively alter the response to flagellin. Our results, support the conclusion that flagellin is an effective adjuvant in the presence of prior immunity to flagellin.

Figure 4:
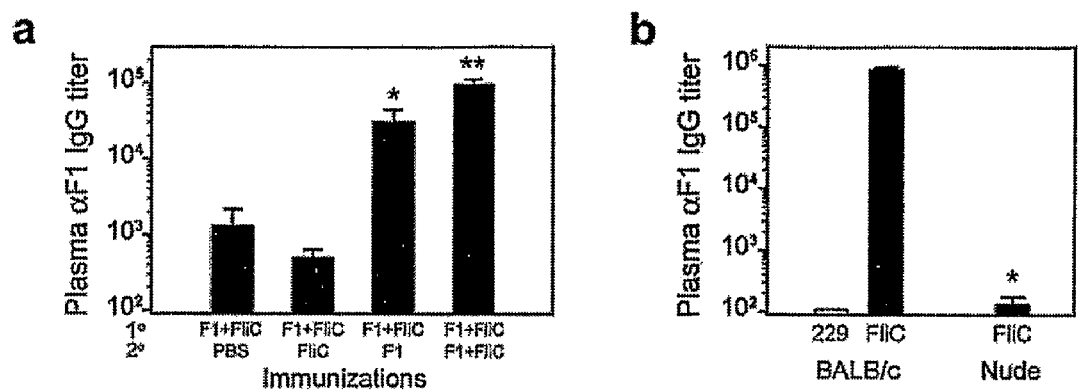
FIGS. 4a to 4b show that flagellin stimulates antigen-specific responses and requires T cells. (Panel a) Groups of 7 female BALB/c mice were immunized i.n. with 10 µg F1 antigen+1 µg flagellin (FliC) and boosted at 4 weeks with PBS, 1 µg FliC alone, 10 µg F1 alone or 10 µg F1+1 µg FliC. Plasma was collected 3 weeks after boosting for analysis by ELISA. * indicates statistical significance over animals boosted with PBS or FliC alone and ** indicates that boosting with F1+FliC results in antibody titers statistically greater than F1 antigen alone ($p<0.01$). Bars represent mean antibody titers ±s.e.m. (Panel b) A group of 7 athymic nude mice (BALB/cAnNCr-nu/nu) was immunized and boosted i.n. with 10 µg F1+1 µg FliC. Plasma was collected 2 weeks post-boost for analysis of anti-F1 IgG titers by ELISA. * indicates statistical significance compared to normal BALB/c mice immunized in an identical manner ($p<0.001$).

The adjuvant effect of flagellin stimulates antigen-specific responses and is dependent on T lymphocytes. The development of immunological memory is an essential feature of an effective vaccine, preparing the immune system to respond rapidly following subsequent exposure to the antigen during infection. To evaluate the requirement for flagellin stimulation in the secondary immunization, four groups of BALB/c mice were immunized with F1 antigen and flagellin and subsequently boosted with PBS, flagellin alone, F1 antigen alone, or flagellin and F1 (FIG. 4, panel a). F1-specific IgG titers in mice boosted with PBS or flagellin alone remained between 500-1100, values that are typical for post-primary responses. However, mice that received F1 antigen alone in the secondary immunization had dramatically increased anti-F1 IgG titers. Although flagellin was not required in the boost, there was a significant increase in anti-F1 antibody titers when flagellin was present. These findings are analogous to those reported in Pasare and Medzhitov (2004) *Immunity* 21:733-741 using LPS as an adjuvant. The authors suggested that once CD4$^+$"memory is established using LPS as an adjuvant, TLR stimulation is no longer required for activation of these lymphocytes. Although the memory response in our system remains to be fully characterized, the lack of an F1-specific IgG response in athymic nude mice (BALB/cAnNCr-nu/nu) immunized with flagellin and F1 (FIG. 4, panel b) demonstrates a requirement for T cells in the humoral response to this vaccine.

TNF-α, IL-6 and interferons are not required for the adjuvant effects of flagellin. Previously, it was determined that flagellin induces high levels of TNF-α"and IL-6 in the lung (Example 1; Honko and Mizel (2004) *Infect. Immun.* 72, 6676-6679). Therefore, the role of these cytokines in the adjuvant activity of flagellin was evaluated. TNF-α"is a pleiotropic cytokine that promotes dendritic cell maturation (Banchereau et al. (2000) *Annu. Rev. Immunol.* 18, 767-811). As shown in FIG. 5, panel a, the anti-F1 antibody response remains extremely high in these mice, indicating that TNF-α"is not required for the adjuvant effect of flagellin. However, flagellin-stimulated TNF-α"production appears to enhance the antibody response against F1 antigen, as the titers in TNFR$^{-/-}$"mice were reduced approximately two-fold relative to wild-type B6; 129 mice. The role of IL-6, a cytokine that promotes B cell proliferation and differentiation (Kaminura et al. (2003) *Rev. Physiol Biochem. Pharmacol.* 149:1-38), in the adjuvant activity of flagellin was evaluated using IL-6$^{-/-}$"mice. There was no defect in anti-F1 IgG production in these mice following immunization with F1 and FliC (FIG. 5, panel b), indicating that this cytokine is also not essential for the adjuvant effect of flagellin.

In vitro, flagellin stimulates nitric oxide and interferon-β" (IFN-β) production via signaling through functional TLR5/4 heteromeric complexes (Mizel et al. (2003) *J. Immunol.* 170: 6217-6223). C3H/HeJ mice, which possess a nonfunctional mutant TLR4 (Poltorak et al. (1998) *Science* 282:2085-2088), provide a model to separate the effects of TLR5/4 heteromeric and TLR5/5 homomeric signaling in vivo. In the lung, flagellin-stimulated production of TNF-α, IL-6, G-CSF (granulocyte colony stimulating factor), keratinocyte-derived chemokine (KC), macrophage inflammatory protein 2 (MIP-2) and MIP-1α"was not disrupted in C3H/HeJ mice (Example 1; Honko and Mizel (2004) *Infect. Immun.* 72:6676-6679); however, interferon production was not evaluated. Type I IFNs are proposed to link innate and adaptive immune responses by stimulating the upregulation of MHC and costimulatory molecules on antigen-presenting cells (Le Bon and Tough (2002) *Curr. Opin. Immunol.* 14:432-436). To determine the role of TLR5/4 signaling on the adjuvant effect of flagellin, anti-F1 antibody titers in C3H/HeJ mice were compared to their wild-type counterpart, C3H/HeN mice (FIG. 5, panel c), following immunization with F1 antigen and flagellin. As there was no defect in antibody production, signaling via TLR5/4 complexes is not required for the adjuvant effects of flagellin. The role of interferons in the adjuvant activity of flagellin was evaluated directly by determining antibody responses in mice lacking either type I interferon signaling (IFNα/βR$^{-/-}$) or the ability to produce interferon-γ"(IFNγ$^{-/-}$) (FIG. 5, panels d and e). As both strains of mice responded in a manner similar to wild-type mice immunized with F1 antigen and flagellin, interferons are also not required for the adjuvant effect of flagellin.

Flagellin promotes a protective response for intranasal challenge with *Yersinia pestis* CO92. The fundamental test of a vaccine is the ability to provide protection against challenge with a pathogen. As a model for respiratory infection, immunized and control mice were challenged intranasally with virulent *Y. pestis* CO92. To ensure that vaccination induced adequate protection, a challenge dose of 150 times the lethal dose 50% ($LD_{50}$) for i.n. infection with *Y. pestis* was selected on the basis of recommendations from a recent Plague Vaccine Workshop sponsored by the NIAID and the FDA (Oct. 13-14, 2004). BALB/c mice immunized and boosted i.n. with flagellin and F1 had a 93% survival rate, versus only 7% in the control group (FIG. 6, panel a), following challenge with a dose equivalent to $100\times LD_{50}$. B cell-deficient $IgH^{-/-}$"mice were used to evaluate the B cell/antibody dependence of the protective response (FIG. 6, panel b). All control and immunized mice succumbed to *Y. pestis* infection at a dose of approximately $150\times LD_{50}$, indicating that protection at this challenge dose is B cell-mediated and thus presumably antibody-mediated. Previously, Elvin et al. examined the role of type 1 effector functions in protection from *Y. pestis* infection using $Stat4^{-/-}$"animals that have defective IL-12 and IFN-γ-mediated cellular immune responses (Elvin and Williamson (2004) *Microb. Patho.* 37:177-184). Whereas immunized $Stat4^{-/-}$"mice produced similar levels of anti-F1 and anti-V IgG as their wild-type counterpart, these animals were less protected from high dose challenge. To address the role of IFN-γ-mediated protection following intranasal challenge in our system, groups of $IFN\text{-}\gamma^{-/-}$"and wild-type C57BL/6 mice were immunized and boosted with F1 antigen and flagellin prior to challenge with $150\times LD_{50}$ *Y. pestis*. Wild-type C57BL/6 mice were completely protected by i.n. immunization with flagellin and F1, versus only 10% of controls (FIG. 6, panel c). Immunized $IFN\text{-}\gamma^{-/-}$"mice had 80% survival following challenge (FIG. 6, panel d), indicating that IFN-γ-mediated responses are not required for protection. As these animals had high titers of anti-F1 IgG, these results confirm the importance of F1-specific antibodies in protection from *Y. pestis* infection and support the utility of circulating IgG titers as a correlate of protective efficacy. The observation that two $IFN\gamma^{-/-}$"mice succumbed to infection suggests that IFN-γ"may augment antibody-mediated protection from *Y. pestis*, possibly through the promotion of the respiratory burst in phagocytes.

Flagellin is an effective adjuvant in nonhuman primates. In view of the ability of flagellin to promote protective adaptive immune responses in murine models, we next evaluated the effectiveness of flagellin as an adjuvant in nonhuman primates. A recombinant fusion protein consisting of the F1 and V antigens of *Y. pestis* was used for immunization of female cynomolgus macaques. Groups of 6 monkeys were immunized with 150 µg F1/V fusion and 50 µg flagellin i.n. or intramuscularly (i.m.). Additional control animals (n=3) received PBS by both routes. Prior to immunization, the monkeys exhibited anti-flagellin antibody titers of approximately $9.8 \times 10^4$. Monkeys immunized with flagellin exhibited no change in body temperature or plasma TNF-α"levels during the first 24 h following immunization, and no observable inflammation occurred at the site of injection. Animals were boosted in an identical manner at four weeks and plasma anti-F1/V IgG titers were determined two weeks later (FIG. 7). Immunized monkeys exhibited a striking increase in F1/V-specific antibody titers. No antigen-specific IgE was detected. These results clearly establish that flagellin is an effective adjuvant for the development of an antibody response in nonhuman primates, even in the presence of circulating anti-flagellin antibodies.

EXAMPLE 4

*Yersinia pestis* Antigens and Vaccines

A fusion protein to induce an immune response against *Yersinia pestis* is produced in a like manner as described in Example 2, with a *Y. pestis* V antigen, a *Y. pestis* F1 antigen, or a fusion peptide thereof. Such fusion proteins can be used to induce an immune response, optionally a protective immune response, as described herein. Optionally, the response is a mucosal immune response. Specific non-limiting examples of suitable fusion proteins are:

```
Example A: FliC/F1/V amino acid sequence
(SEQ ID NO: 1)
  1 MAQVINTNSL SLLTQNNLNK SQSSLSSAIE RLSSGLRINS
    AKDDAAGQAI

51 ANRFTSNIKG LTQASRNAND GISIAQTTEG ALNEINNNLQ
    RVRELSVQAT

101 NGTNSDSDLK SIQDEIQQRL EEIDRVSNQT QFNGVKVLSQ
    DNQMKIQVGA

151 NDGETITIDL QKIDVKSLGL DGFNVNGPKE ATVGDLKSSF
    KNVTGRSMAD

201 LTASTTATAT LVEPARITLT YKEGAPITIM DNGNIDTELL
    VGTLTLGGYK

251 TGTTSTSVNF TDAAGDPMYL TFTSQDGNNH QFTTKVIGKD
    SRDFDISPKV

301 NGENLVGDDV VLATGSQDFF VRSIGSKGGK LAAGKYTDAV
    TVTVSNQGSI

351 EGRNRAYEQN PQHFIEDLEK VRVEQLTGHG SSVLEELVQL
    VKDKNIDISI

401 KYDPRKDSEV FANRVITDDI ELLKKILAYF LPEDAILKGG
    HYDNQLQNGI

451 KRVKEFLESS PNTQWELRAF MAVMHFSLTA DRIDDDILKV
    IVDSMNHHGD

501 ARSKLREELA ELTAELKIYS VIQAEINKHL SSSGTINIHD
    KSINLMDKNL

551 YGYTDEEIFK ASAEYKILEK MPQTTIQVDG SEKKIVSIKD
    FLGSENKRTG

601 ALGNLKNSYS YNKDNNELSH FATTCSDKSR PLNDLVSQKT
    TQLSDITSRF

651 NSAIEALNRF IQKYDSVMQR LLDDTSGKRS ATGDKITLAG
    KTMFIDKTAS

701 GVSTLINEDA AAKKSTANP LASIDSALSK VDAVRSSLGA
    IQNRFDSAIT

751 NLGNTVTNLN SARSRIEDAD YATEVSNMSK AQILQQAGTS
    VLAQANQVPQ

801 NVLSLLRLEH HHHHH*

Example B: FliC/F1 amino acid sequence
(SEQ ID NO: 2)
  1 MAQVINTNSL SLLTQNNLNK SQSSLSSAIE RLSSGLRINS
    AKDDAAGQAI

51 ANRFTSNIKG LTQASRNAND GISIAQTTEG ALNEINNNLQ
    RVRELSVQAT

101 NGTNSDSDLK SIQDEIQQRL EEIDRVSNQT QFNGVKVLSQ
    DNQMKIQVGA

151 NDGETITIDL QKIDVKSLGL DGFNVNGPKE ATVGDLKSSF
    KNVTGRSMAD

201 LTASTTATAT LVEPARITLT YKEGAPITIM DNGNIDTELL
    VGTLTLGGYK

251 TGTTSTSVNF TDAAGDPMYL TFTSQDGNNH QFTTKVIGKD
    SRDFDISPKV

301 NGENLVGDDV VLATGSQDFF VRSIGSKGGK LAAGKYTDAV
    TVTVSNQRSA

351 TGDKITLAGK TMFIDKTASG VSTLINEDAA AAKKSTANPL
    ASIDSALSKV

401 DAVRSSLGAI QNRFDSAITN LGNTVTNLNS ARSRIEDADY
    ATEVSNMSKA

451 QILQQAGTSV LAQANQVPQN VLSLLRLEHH HHHH*

EXAMPLE C: FliC/V amino acid sequence
(SEQ ID NO: 3)
  1 MAQVINTNSL SLLTQNNLNK SQSSLSSAIE RLSSGLRINS
    AKDDAAGQAI

51 ANRFTSNIKG LTQASRNAND GISIAQTTEG ALNEINNNLQ
    RVRELSVQAT

101 NGTNSDSDLK SIQDEIQQRL EEIDRVSNQT QFNGVKVLSQ
    DNQMKIQVGA

151 NDGETITIDL QKIDVKSLGL DGFNVNGPKE ATVGDLKSSF
    KNVTGRSMIR

201 AYEQNPQHFI EDLEKVRVEQ LTGHGSSVLE ELVQLVKDKN
    IDISIKYDPR

251 KDSEVFANRV ITDDIELLKK ILAYFLPEDA ILKGGHYDNQ
    LQNGIKRVKE

301 FLESSPNTQW ELRAFMAVMH FSLTADRIDD DILKVIVDSM
    NHHGDARSKL

351 REELAELTAE LKIYSVIQAE INKHLSSSGT INIHDKSINL
    MDKNLYGYTD

401 EEIFKASAEY KILEKMPQTT IQVDGSEKKI VSIKDFLGSE
    NKRTGALGNL

451 KNSYSYNKDN NELSHFATTC SDKSRPLNDL VSQKTTQLSD
    ITSRFNSAIE
```

```
-continued
501 ALNRFIQKYD SVMQRLLDDT SGK<u>RSATGDK</u> ITLAGKTMFI
    DKTASGVSTL

551 INEDAAAAKK STANPLASID SALSKVDAVR SSLGAIQNRF
    DSAITNLGNT

601 VTNLNSARSR IEDADYATEV SNMSKAQILQ QAGTSVLAQA
    NQVPQNVLSL

651 LRLEHHHHHH *
Note:
FliC obtained from S. enteritidis. In each of these fusion
proteins, the N terminal constant region of FliC ends at amino
acid residue 198, and the C terminal constant region (the first
seven amino acids of which is denoted in bold and underlined)
begins at amino acid residue 679 of Example A (SEQ ID NO: 1),
amino acid residue 348 of Example B (SEQ ID NO: 2), and amino
acid residue 524 of Example C (SEQ ID NO: 3).
```

EXAMPLE 5

Biological Activity of a Fusion Peptide Containing Flagellin and the F1 and V Antigens of *Yersinia pestis*

Figure 8:
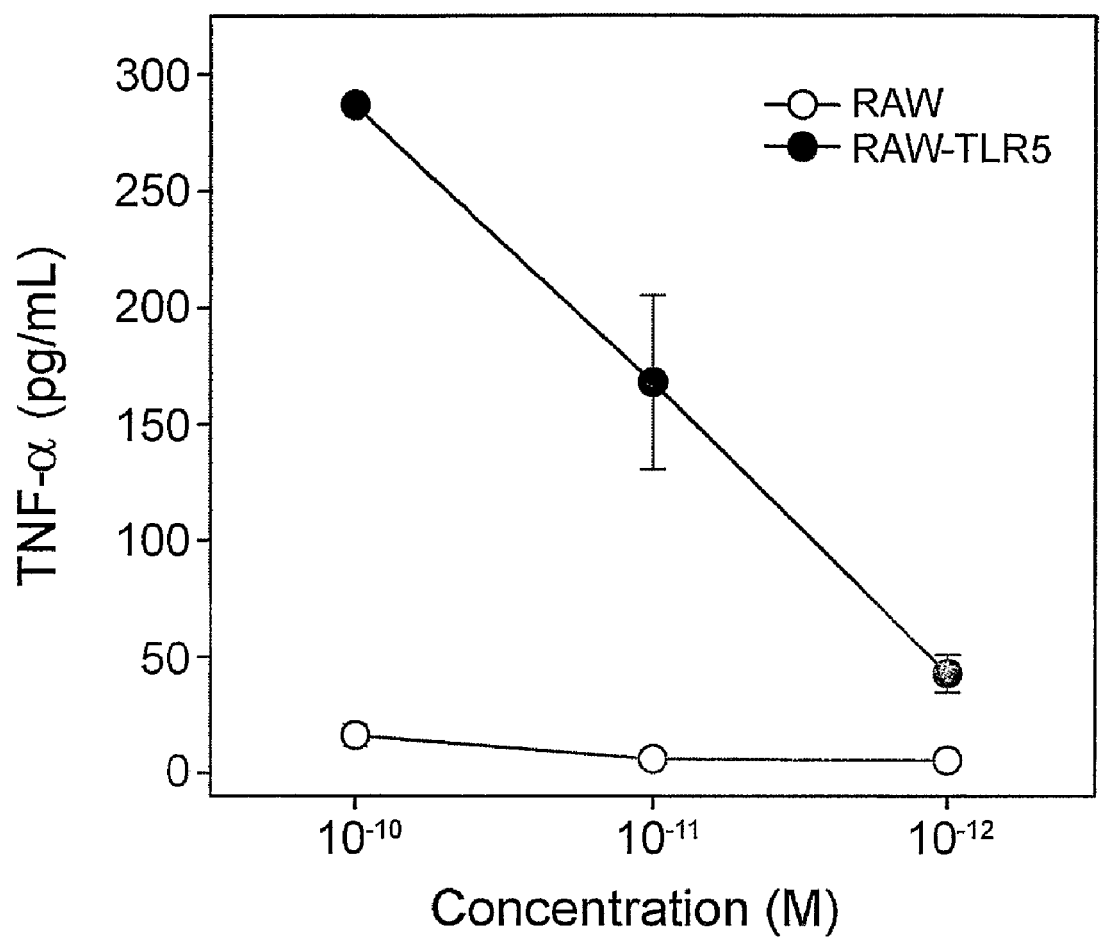
FIG. 8 shows that a fusion protein containing flagellin and the Yersinia pestis F1 and V proteins retains flagellin biological activity.

To prepare an expression plasmid encoding flagellin and *Yersinia pestis* F1 and V antigens as a single protein, the majority of the nucleotide sequence encoding the hypervariable region of the *S. enteritidis* flagellin was removed and replaced with the F1 and V sequences in tandem separated by an eighteen nucleotide bridge encoding 6 amino acids (see Example A, SEQ ID NO:1, above). The recombinant protein was produced in BL21 cells and purified by affinity chromatography on a metal affinity resin. Endotoxin and contaminating nucleic acid were removed using an Acrodisc chromatography filter. To determine if the resultant protein retained flagellin bioactivity, TLR5-negative and TLR5-positive RAW264.7 cells were incubated with the trifusion protein and the extent of tumor necrosis factor-α production was determined. The TLR5-negative RAW cells were used to control for any contaminating factors that might have an effect in this assay. As shown in FIG. 8, a fusion protein containing flagellin and the *Yersinia pestis* F1 and V proteins retains flagellin biological activity in TLR5-positive cells. The protein did not signal in TLR5-negative RAW264.7 cells.

Toll-like receptor 5 (TLR5)-negative RAW264.7 cells or TLR5-positive RAW264.7 cells (a cell line created by stably transfecting RAW264.7 cells with a construct encoding a TLR5-enhanced yellow fluorescent protein) were incubated with increasing concentrations of a fusion protein encoding flagellin and the F1 and V proteins of *Y. pestis* for 4 hours and then the culture medium was assayed by ELISA for the content of TNF-α.

To determine if flagellin+F1+V or a single protein containing all three protects against a lethal challenge with *Y. pestis* CO92, C3H/HeJ mice were immunized and boosted with phosphate buffered saline only (PBS) or a vaccine containing three proteins-1 mg flagellin+5 mg each F1 and V or a vaccine containing a single protein containing flagellin, F1, and V (flagellin/F1/V; 10 mg). The mice were boosted after 4 weeks with the same regimens and then challenged with approximately 150 $LD_{50}$ of *Y. pestis* CO92. The mice were bled prior to the challenge and anti-F1 IgG titers were determined by ELISA. As shown in Table 2, flagellin+F1 and V antigens of *Yersinia pestis* or a fusion protein containing flagellin and the F1 and V antigens of *Yersinia pestis* provides complete protection against a lethal respiratory challenge with *Yersinia pestis*.

TABLE 2

Results of protection studies of mice immunized with flagellin + F1 and V antigens of *Y. pestis* or a fusion protein containing flagellin and the F1 and V antigens of *Y. pestis* against a lethal respiratory challenge with *Y. pestis*.

| Immunization | Anti-F1 IgG titer | Anti-V IgG titer | Survival Number | Percent |
|---|---|---|---|---|
| PBS | $6.6 \times 10^2$ | $1.2 \times 10^3$ | 0/10 | 0 |
| Flagellin + F1 + V | $4.5 \times 10^6$ | $4.2 \times 10^6$ | 10/10 | 100 |
| Flagellin/F1/V | $5 \times 10^6$ | $6.3 \times 10^6$ | 4/4 | 100 |

The foregoing is illustrative of the present invention, and is not to be taken as limiting thereof. The invention is defined by the following claims, with equivalents of the claims to be included therein.

That which is claimed is:

1. An isolated fusion protein comprising:
   (a) an isolated flagellin adjuvant comprising:
      (i) a flagellin N-terminal constant region; and
      (ii) a flagellin C-terminal constant region; and
   (b) a *Yersinia pestis* antigen between the flagellin N-terminal constant region and the flagellin C-terminal constant region, wherein the *Y. pestis* antigen comprises *Y. pestis* F1 antigen, *Y. pestis* V antigen, or a fusion peptide of *Y. pestis* F1 antigen and *Y. pestis* V. antigen; and
   wherein the flagellin N-terminal constant region and/or the flagellin C-terminal constant region of the isolated flagellin adjuvant comprises a TLR5 recognition site and is able to activate the TLR5 pathway.

2. The fusion protein of claim 1, wherein the flagellin adjuvant comprises a deleted flagellin hypervariable region or the flagellin hypervariable region is absent from the flagellin adjuvant.

3. The fusion protein of claim 1, wherein the *Y. pestis* antigen is inserted (i) within the flagellin hypervariable region, (ii) between the flagellin N-terminal constant region and the flagellin hypervariable region, or (iii) between the flagellin C-terminal constant region and the flagellin hypervariable region.

4. The fusion protein of claim 1, wherein the *Yersinia pestis* antigen is selected from the group consisting of *Y. pestis* F1 antigen, *Y. pestis* V antigen, and a fusion peptide of *Y. pestis* F1 antigen and *Y. pestis* V. antigen.

5. An immunogenic composition comprising the fusion protein of claim 1 in a pharmaceutically acceptable carrier.

6. A method of producing an immune response against *Yersinia pestis* in a mammalian subject, the method comprising administering the fusion protein of claim 1 to the subject in an amount effective to produce the immune response in the mammalian subject against *Yersinia pestis*.

7. The method of claim 6, wherein the administering step is carried out by delivering the fusion protein to a mucosal surface.

8. The method of claim 7, wherein the administering step is carried out by intranasal or inhalation administration.

9. The method of claim 6, wherein the human subject at least 50 years old.

10. An immunogenic composition for mucosal administration, comprising the isolated fusion protein of claim 1 in a pharmaceutically acceptable carrier.

11. The immunogenic composition of claim 10, wherein the *Yersinia pestis* antigen is selected from the group consisting of *Y. pestis* F1 antigen, *Y. pestis* V antigen, and a fusion peptide of *Y. pestis* F1 antigen and *Y. pestis* V. antigen.

12. The immunogenic composition of claim 10, further comprising a second *Yersinia pestis* antigen not coupled to the flagellin adjuvant.

13. A method of producing an immune response against *Yersinia pestis* in a human subject, the method comprising mucosally administering the composition of claim 10 to the human subject in an amount effective to produce the immune response against *Yersinia pestis* in the human subject.

14. The method of claim 13, wherein the administering step is carried out by intranasal or inhalation administration.

15. The method of claim 13, wherein said subject is a human subject at least 50 years old.

16. A method of producing an immune response against *Yersinia pestis* in a mammalian subject, the method comprising administering the immunogenic composition of claim 5 to the subject in an amount effective to produce the immune response in the mammalian subject against *Yersinia pestis*.

17. An isolated fusion protein comprising:
   (a) a flagellin adjuvant comprising:
      (i) a flagellin N-terminal constant region; and
      (ii) a flagellin C-terminal constant region; and
   (b) a *Yersinia pestis* antigen, wherein the antigen is a fusion peptide of *Y. pestis* F1 antigen and *Y. pestis* V antigen and is inserted within the flagellin hypervariable region between the flagellin N-terminal constant region and the flagellin C-terminal constant region.

18. The isolated fusion protein of claim 17, wherein the fusion protein comprises the amino acid sequence of SEQ ID NO:1.

19. An immunogenic composition comprising the fusion protein of claim 17 in a pharmaceutically acceptable carrier.

20. A method of producing an immune response against *Yersinia pestis* in a mammalian subject, the method comprising administering the immunogenic composition of claim 17 to the subject in an amount effective to produce the immune response in the mammalian subject against *Yersinia pestis*.

21. A method of producing an immune response against *Yersinia pestis* in a mammalian subject, the method comprising administering the immunogenic composition of claim 19 to the subject in an amount effective to produce the immune response in the mammalian subject against *Yersinia pestis*.

* * * * *

SEQUENCE LISTING

<160> NUMBER OF SEQ ID NOS: 4

<210> SEQ ID NO 1
<211> LENGTH: 815
<212> TYPE: PRT
<213> ORGANISM: Artificial
<220> FEATURE:
<223> OTHER INFORMATION: FliC/F1/V fusion protein

<400> SEQUENCE: 1

```
Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60
```

```
Ser Arg Asn Ala Asn Asp Gly Ile Ser Ile Ala Gln Thr Thr Glu Gly
 65                  70                  75                  80

Ala Leu Asn Glu Ile Asn Asn Leu Gln Arg Val Arg Glu Leu Ser
             85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Ile Asp Arg Val Ser Asn
            115                 120                 125

Gln Thr Gln Phe Asn Gly Val Lys Val Leu Ser Gln Asp Asn Gln Met
        130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Gly Pro Lys Glu Ala Thr Val Gly Asp Leu Lys Ser Ser Phe Lys Asn
            180                 185                 190

Val Thr Gly Arg Ser Met Ala Asp Leu Thr Ala Ser Thr Ala Thr
        195                 200                 205

Ala Thr Leu Val Glu Pro Ala Arg Ile Thr Leu Thr Tyr Lys Glu Gly
    210                 215                 220

Ala Pro Ile Thr Ile Met Asp Asn Gly Asn Ile Asp Thr Glu Leu Leu
225                 230                 235                 240

Val Gly Thr Leu Thr Leu Gly Gly Tyr Lys Thr Gly Thr Thr Ser Thr
                245                 250                 255

Ser Val Asn Phe Thr Asp Ala Ala Gly Asp Pro Met Tyr Leu Thr Phe
            260                 265                 270

Thr Ser Gln Asp Gly Asn Asn His Gln Phe Thr Thr Lys Val Ile Gly
        275                 280                 285

Lys Asp Ser Arg Asp Phe Asp Ile Ser Pro Lys Val Asn Gly Glu Asn
290                 295                 300

Leu Val Gly Asp Asp Val Val Leu Ala Thr Gly Ser Gln Asp Phe Phe
305                 310                 315                 320

Val Arg Ser Ile Gly Ser Lys Gly Gly Lys Leu Ala Ala Gly Lys Tyr
                325                 330                 335

Thr Asp Ala Val Thr Val Thr Val Ser Asn Gln Gly Ser Ile Glu Gly
            340                 345                 350

Arg Asn Arg Ala Tyr Glu Gln Asn Pro Gln His Phe Ile Glu Asp Leu
        355                 360                 365

Glu Lys Val Arg Val Glu Gln Leu Thr Gly His Gly Ser Ser Val Leu
370                 375                 380

Glu Glu Leu Val Gln Leu Val Lys Asp Lys Asn Ile Asp Ile Ser Ile
385                 390                 395                 400

Lys Tyr Asp Pro Arg Lys Asp Ser Glu Val Phe Ala Asn Arg Val Ile
                405                 410                 415

Thr Asp Asp Ile Glu Leu Leu Lys Lys Ile Leu Ala Tyr Phe Leu Pro
            420                 425                 430

Glu Asp Ala Ile Leu Lys Gly Gly His Tyr Asp Asn Gln Leu Gln Asn
        435                 440                 445

Gly Ile Lys Arg Val Lys Glu Phe Leu Glu Ser Pro Asn Thr Gln
450                 455                 460

Trp Glu Leu Arg Ala Phe Met Ala Val Met His Phe Ser Leu Thr Ala
465                 470                 475                 480
```

Asp Arg Ile Asp Asp Ile Leu Lys Val Ile Val Asp Ser Met Asn
            485                 490                 495

His His Gly Asp Ala Arg Ser Lys Leu Arg Glu Glu Leu Ala Glu Leu
            500                 505                 510

Thr Ala Glu Leu Lys Ile Tyr Ser Val Ile Gln Ala Glu Ile Asn Lys
            515                 520                 525

His Leu Ser Ser Gly Thr Ile Asn Ile His Asp Lys Ser Ile Asn
            530                 535                 540

Leu Met Asp Lys Asn Leu Tyr Gly Tyr Thr Asp Glu Glu Ile Phe Lys
545                 550                 555                 560

Ala Ser Ala Glu Tyr Lys Ile Leu Glu Lys Met Pro Gln Thr Thr Ile
                565                 570                 575

Gln Val Asp Gly Ser Glu Lys Lys Ile Val Ser Ile Lys Asp Phe Leu
            580                 585                 590

Gly Ser Glu Asn Lys Arg Thr Gly Ala Leu Gly Asn Leu Lys Asn Ser
            595                 600                 605

Tyr Ser Tyr Asn Lys Asp Asn Asn Glu Leu Ser His Phe Ala Thr Thr
            610                 615                 620

Cys Ser Asp Lys Ser Arg Pro Leu Asn Asp Leu Val Ser Gln Lys Thr
625                 630                 635                 640

Thr Gln Leu Ser Asp Ile Thr Ser Arg Phe Asn Ser Ala Ile Glu Ala
            645                 650                 655

Leu Asn Arg Phe Ile Gln Lys Tyr Asp Ser Val Met Gln Arg Leu Leu
            660                 665                 670

Asp Asp Thr Ser Gly Lys Arg Ser Ala Thr Gly Asp Lys Ile Thr Leu
            675                 680                 685

Ala Gly Lys Thr Met Phe Ile Asp Lys Thr Ala Ser Gly Val Ser Thr
            690                 695                 700

Leu Ile Asn Glu Asp Ala Ala Ala Lys Lys Ser Thr Ala Asn Pro
705                 710                 715                 720

Leu Ala Ser Ile Asp Ser Ala Leu Ser Lys Val Asp Ala Val Arg Ser
            725                 730                 735

Ser Leu Gly Ala Ile Gln Asn Arg Phe Asp Ser Ala Ile Thr Asn Leu
            740                 745                 750

Gly Asn Thr Val Thr Asn Leu Asn Ser Ala Arg Ser Arg Ile Glu Asp
            755                 760                 765

Ala Asp Tyr Ala Thr Glu Val Ser Asn Met Ser Lys Ala Gln Ile Leu
            770                 775                 780

Gln Gln Ala Gly Thr Ser Val Leu Ala Gln Ala Asn Gln Val Pro Gln
785                 790                 795                 800

Asn Val Leu Ser Leu Leu Arg Leu Glu His His His His His
            805                 810                 815

<210> SEQ ID NO 2
<211> LENGTH: 484
<212> TYPE: PRT
<213> ORGANISM: Artificial
<220> FEATURE:
<223> OTHER INFORMATION: FliC/F1 fusion protein

<400> SEQUENCE: 2

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

-continued

```
Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
 50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ser
                 85                  90                  95

Val Gln Ala Thr Asn Gly Thr Asn Ser Asp Ser Asp Leu Lys Ser Ile
                100                 105                 110

Gln Asp Glu Ile Gln Gln Arg Leu Glu Glu Ile Asp Arg Val Ser Asn
            115                 120                 125

Gln Thr Gln Phe Asn Gly Val Lys Val Leu Ser Gln Asp Asn Gln Met
        130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Gly Pro Lys Glu Ala Thr Val Gly Asp Leu Lys Ser Ser Phe Lys Asn
            180                 185                 190

Val Thr Gly Arg Ser Met Ala Asp Leu Thr Ala Ser Thr Ala Thr
        195                 200                 205

Ala Thr Leu Val Glu Pro Ala Arg Ile Thr Leu Thr Tyr Lys Glu Gly
    210                 215                 220

Ala Pro Ile Thr Ile Met Asp Asn Gly Asn Ile Asp Thr Glu Leu Leu
225                 230                 235                 240

Val Gly Thr Leu Thr Leu Gly Gly Tyr Lys Thr Gly Thr Thr Ser Thr
                245                 250                 255

Ser Val Asn Phe Thr Asp Ala Ala Gly Asp Pro Met Tyr Leu Thr Phe
            260                 265                 270

Thr Ser Gln Asp Gly Asn Asn His Gln Phe Thr Thr Lys Val Ile Gly
        275                 280                 285

Lys Asp Ser Arg Asp Phe Asp Ile Ser Pro Lys Val Asn Gly Glu Asn
    290                 295                 300

Leu Val Gly Asp Asp Val Val Leu Ala Thr Gly Ser Gln Asp Phe Phe
305                 310                 315                 320

Val Arg Ser Ile Gly Ser Lys Gly Gly Lys Leu Ala Ala Gly Lys Tyr
                325                 330                 335

Thr Asp Ala Val Thr Val Thr Val Ser Asn Gln Arg Ser Ala Thr Gly
            340                 345                 350

Asp Lys Ile Thr Leu Ala Gly Lys Thr Met Phe Ile Asp Lys Thr Ala
        355                 360                 365

Ser Gly Val Ser Thr Leu Ile Asn Glu Asp Ala Ala Ala Lys Lys
    370                 375                 380

Ser Thr Ala Asn Pro Leu Ala Ser Ile Asp Ser Ala Leu Ser Lys Val
385                 390                 395                 400

Asp Ala Val Arg Ser Ser Leu Gly Ala Ile Gln Asn Arg Phe Asp Ser
                405                 410                 415

Ala Ile Thr Asn Leu Gly Asn Thr Val Thr Asn Leu Asn Ser Ala Arg
            420                 425                 430

Ser Arg Ile Glu Asp Ala Asp Tyr Ala Thr Glu Val Ser Asn Met Ser
        435                 440                 445

Lys Ala Gln Ile Leu Gln Gln Ala Gly Thr Ser Val Leu Ala Gln Ala
```

```
                      450             455             460
Asn Gln Val Pro Gln Asn Val Leu Ser Leu Leu Arg Leu Glu His His
465                     470             475                 480

His His His His

<210> SEQ ID NO 3
<211> LENGTH: 660
<212> TYPE: PRT
<213> ORGANISM: Artificial
<220> FEATURE:
<223> OTHER INFORMATION: FliC/V fusion protein

<400> SEQUENCE: 3

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ser Asn Ile Lys Gly Leu Thr Gln Ala
50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Gly Pro Lys Glu Ala Thr Val Gly Asp Leu Lys Ser Ser Phe Lys Asn
            180                 185                 190

Val Thr Gly Arg Ser Met Ile Arg Ala Tyr Glu Gln Asn Pro Gln His
        195                 200                 205

Phe Ile Glu Asp Leu Glu Lys Val Arg Val Glu Gln Leu Thr Gly His
    210                 215                 220

Gly Ser Ser Val Leu Glu Glu Leu Val Gln Leu Val Lys Asp Lys Asn
225                 230                 235                 240

Ile Asp Ile Ser Ile Lys Tyr Asp Pro Arg Lys Asp Ser Glu Val Phe
                245                 250                 255

Ala Asn Arg Val Ile Thr Asp Asp Ile Glu Leu Leu Lys Lys Ile Leu
            260                 265                 270

Ala Tyr Phe Leu Pro Glu Asp Ala Ile Leu Lys Gly Gly His Tyr Asp
        275                 280                 285

Asn Gln Leu Gln Asn Gly Ile Lys Arg Val Lys Glu Phe Leu Glu Ser
    290                 295                 300

Ser Pro Asn Thr Gln Trp Glu Leu Arg Ala Phe Met Ala Val Met His
305                 310                 315                 320

Phe Ser Leu Thr Ala Asp Arg Ile Asp Asp Ile Leu Lys Val Ile
                325                 330                 335
```

```
Val Asp Ser Met Asn His His Gly Asp Ala Arg Ser Lys Leu Arg Glu
        340                 345                 350

Glu Leu Ala Glu Leu Thr Ala Glu Leu Lys Ile Tyr Ser Val Ile Gln
        355                 360                 365

Ala Glu Ile Asn Lys His Leu Ser Ser Ser Gly Thr Ile Asn Ile His
        370                 375                 380

Asp Lys Ser Ile Asn Leu Met Asp Lys Asn Leu Tyr Gly Tyr Thr Asp
385                 390                 395                 400

Glu Glu Ile Phe Lys Ala Ser Ala Glu Tyr Lys Ile Leu Glu Lys Met
                405                 410                 415

Pro Gln Thr Thr Ile Gln Val Asp Gly Ser Glu Lys Lys Ile Val Ser
                420                 425                 430

Ile Lys Asp Phe Leu Gly Ser Glu Asn Lys Arg Thr Gly Ala Leu Gly
                435                 440                 445

Asn Leu Lys Asn Ser Tyr Ser Tyr Asn Lys Asp Asn Asn Glu Leu Ser
        450                 455                 460

His Phe Ala Thr Thr Cys Ser Asp Lys Ser Arg Pro Leu Asn Asp Leu
465                 470                 475                 480

Val Ser Gln Lys Thr Thr Gln Leu Ser Asp Ile Thr Ser Arg Phe Asn
                485                 490                 495

Ser Ala Ile Glu Ala Leu Asn Arg Phe Ile Gln Lys Tyr Asp Ser Val
                500                 505                 510

Met Gln Arg Leu Leu Asp Asp Thr Ser Gly Lys Arg Ser Ala Thr Gly
                515                 520                 525

Asp Lys Ile Thr Leu Ala Gly Lys Thr Met Phe Ile Asp Lys Thr Ala
        530                 535                 540

Ser Gly Val Ser Thr Leu Ile Asn Glu Asp Ala Ala Ala Lys Lys
545                 550                 555                 560

Ser Thr Ala Asn Pro Leu Ala Ser Ile Asp Ser Ala Leu Ser Lys Val
                565                 570                 575

Asp Ala Val Arg Ser Ser Leu Gly Ala Ile Gln Asn Arg Phe Asp Ser
                580                 585                 590

Ala Ile Thr Asn Leu Gly Asn Thr Val Thr Asn Leu Asn Ser Ala Arg
                595                 600                 605

Ser Arg Ile Glu Asp Ala Asp Tyr Ala Thr Glu Val Ser Asn Met Ser
        610                 615                 620

Lys Ala Gln Ile Leu Gln Gln Ala Gly Thr Ser Val Leu Ala Gln Ala
625                 630                 635                 640

Asn Gln Val Pro Gln Asn Val Leu Ser Leu Leu Arg Leu Glu His His
                645                 650                 655

His His His His
        660

<210> SEQ ID NO 4
<211> LENGTH: 12
<212> TYPE: PRT
<213> ORGANISM: Artificial
<220> FEATURE:
<223> OTHER INFORMATION: Tumor antigen immunogenicity enhancing peptide
      sequence

<400> SEQUENCE: 4

Gly Ala Val Gln Asn Arg Phe Asn Ser Ala Ile Thr
1               5                   10
```